US009314515B2

(12) United States Patent
Grigoriadis et al.

(10) Patent No.: US 9,314,515 B2
(45) Date of Patent: Apr. 19, 2016

(54) TARGETED TREATMENT FOR PATIENTS WITH ESTROGEN RECEPTOR NEGATIVE AND PROGESTERONE RECEPTOR NEGATIVE BREAST CANCERS

(75) Inventors: Anita Grigoriadis, London (GB); Otavia L. Caballero, Lutherville, MD (US); Andrew John George Simpson, Westport, CT (US)

(73) Assignee: Ludwig Institute for Cancer Research Ltd., New York, NY (US)

( * ) Notice: Subject to any disclaimer, the term of this patent is extended or adjusted under 35 U.S.C. 154(b) by 1111 days.

(21) Appl. No.: 12/989,233

(22) PCT Filed: Apr. 22, 2009

(86) PCT No.: PCT/US2009/002483
§ 371 (c)(1),
(2), (4) Date: Feb. 3, 2011

(87) PCT Pub. No.: WO2009/131673
PCT Pub. Date: Oct. 29, 2009

(65) Prior Publication Data
US 2011/0150935 A1    Jun. 23, 2011

Related U.S. Application Data

(60) Provisional application No. 61/125,521, filed on Apr. 25, 2008.

(51) Int. Cl.
| | |
|---|---|
| A61K 38/02 | (2006.01) |
| A61K 38/17 | (2006.01) |
| A61K 39/00 | (2006.01) |
| C07K 14/47 | (2006.01) |
| G01N 33/574 | (2006.01) |
| G01N 33/74 | (2006.01) |

(52) U.S. Cl.
CPC ......... *A61K 39/0011* (2013.01); *C07K 14/4748* (2013.01); *G01N 33/57415* (2013.01); *G01N 33/743* (2013.01); *G01N 2333/723* (2013.01)

(58) Field of Classification Search
CPC . A61K 39/0011; A61K 38/17; A61K 39/385; C07K 14/4748
See application file for complete search history.

(56) References Cited

U.S. PATENT DOCUMENTS 7,084,239 B1 *   8/2006   Wang et al. ............ 530/300
2006/0275305 A1  12/2006  Bryant

FOREIGN PATENT DOCUMENTS

| WO | WO 96/10577 A1 | 4/1996 |
| WO | WO 96/33739 A1 | 10/1996 |
| WO | WO 2004/031354 A2 | 4/2004 |

OTHER PUBLICATIONS

Fitzgibbons, P.L., et al. Arch Pathol. Lab Med., 124: 966-978, 2000.*
Stevanovic, S., Nature Reviews, 2: 1-7, 2002.*
Davis, I.D., et al., Proc. Natl. Acad. Sci, 101(29): 10697-10702, 2004.*
Braun, S. et al, The Oncologist, 6: 125-132, 2001.*
Odunsi, K., et al. Proc. Natl. Acad. Sci., 104(31): 12837-12842, Jul. 2007.*
Emens, L.A., Expert Rev. Vaccines, 4(60: 829-841, 2005.*
Suri, A., Expert Opin. Biol. Ther., 6(4): 379-389, 2006.*
Nicholaou, T., et al., Immunology and Cell Biology, 84: 303-317, 2006.*
Meek, D.W., et al., Cancer Letters, 324: 126-132, 2012.*
Brichard, V.G., et al. Expert Opin. Biol. Ther., 8(7): 951-968, 2008.*
Krüger et al., Expression of cancer-testis antigen CT7 (MAGE-C1) in breast cancer: an immunohistochemical study with emphasis on prognostic utility. Pathol Oncol Res. 2007;13(2):91-6. Epub Jul. 3, 2007.
Otte et al., MAGE-A gene expression pattern in primary breast cancer. Cancer Res. Sep. 15, 2001;61(18):6682-7.
Sahin et al., Expression of multiple cancer/testis (CT) antigens in breast cancer and melanoma: basis for polyvalent CT vaccine strategies. Int J Cancer. Oct. 29, 1998;78(3):387-9.
Zippelius et al., [Identification of tumor antigens: strategies and perspectives]. Dtsch Med Wochenschr. Aug. 18, 2006;131(33):1809-12. German.
[No Author Listed], Statistical Algorithms Description Document. Affymetrix, Inc. 2002. 28 pages. Available at www.affymetrix.com/support/technical/whitepapers/sadd_whitepaper.pdf, Last accessed Oct. 21, 2011.
Allsopp et al., Comparison of numerous delivery systems for the induction of cytotoxic T lymphocytes by immunization. Eur J Immunol. Aug. 1996;26(8):1951-9.
Almeida et al., CTdatabase: a knowledge-base of high-throughput and curated data on cancer-testis antigens. Nucleic Acids Res. Jan. 2009;37(Database issue):D816-9. Epub Oct. 5, 2008.
Andrade et al., Prognostic impact of cancer/testis antigen expression in advanced stage multiple myeloma patients. Cancer Immun. Feb. 1, 2008;8:2.
Atanackovic et al., Booster vaccination of cancer patients with MAGE-A3 protein reveals long-term immunological memory or tolerance depending on priming. Proc Natl Acad Sci U S A. Feb. 5, 2008;105(5):1650-5. Epub Jan. 23, 2008.
Bandić et al., Expression and possible prognostic role of MAGE-A4, NY-ESO-1, and HER-2 antigens in women with relapsing invasive ductal breast cancer: retrospective immunohistochemical study. Croat Med J. Feb. 2006;47(1):32-41.
Bender et al., LUD 00-009: phase 1 study of intensive course immunization with NY-ESO-1 peptides in HLA-A2 positive patients with NY-ESO-1-expressing cancer. Cancer Immun. Oct. 19, 2007;7:16.
Bennett et al., Help for cytotoxic-T-cell responses is mediated by CD40 signalling. Nature. Jun. 4, 1998;393(6684):478-80.
Bild et al., Oncogenic pathway signatures in human cancers as a guide to targeted therapies. Nature. Jan. 19, 2006;439(7074):353-7. Epub Nov. 6, 2005.

(Continued)

*Primary Examiner* — Alana Harris Dent
*Assistant Examiner* — Anne Holleran
(74) *Attorney, Agent, or Firm* — Wolf, Greenfield & Sacks, P.C.

(57) ABSTRACT

Treatments for estrogen receptor and progesterone receptor negative breast cancer or estrogen receptor, progesterone receptor and c-erbB2 negative (triple negative) breast cancer are provided.

18 Claims, 15 Drawing Sheets

(56) References Cited

OTHER PUBLICATIONS

Boersma et al., A stromal gene signature associated with inflammatory breast cancer. Int J Cancer. Mar. 15, 2008;122(6):1324-32.

Chin et al., Genomic and transcriptional aberrations linked to breast cancer pathophysiologies. Cancer Cell. Dec. 2006;10(6):529-41.

Coulie, Antigens recognized on human tumors by cytolytic T lymphocytes: towards vaccination? Stem Cells. Jul. 1995;13(4):393-403.

Crabb et al., Basal breast cancer molecular subtype predicts for lower incidence of axillary lymph node metastases in primary breast cancer. Clin Breast Cancer. Jun. 2008;8(3):249-56.

Curigliano et al., Immunology and breast cancer: therapeutic cancer vaccines. Breast. Dec. 2007;16 Suppl 2:S20-6. Epub Aug. 13, 2007.

Davis et al., Recombinant NY-ESO-1 protein with ISCOMATRIX adjuvant induces broad integrated antibody and CD4(+) and CD8(+) T cell responses in humans. Proc Natl Acad Sci U S A. Jul. 20, 2004;101(29):10697-702. Epub Jul. 13, 2004

Desmedt et al., TRANSBIG Consortium. Strong time dependence of the 76-gene prognostic signature for node-negative breast cancer patients in the TRANSBIG multicenter independent validation series. Clin Cancer Res. Jun. 1, 2007;13(11):3207-14.

Doane et al., An estrogen receptor-negative breast cancer subset characterized by a hormonally regulated transcriptional program and response to androgen. Oncogene. Jun. 29, 2006;25(28):3994-4008. Epub Feb. 20, 2006.

Fenton et al., Induction of melanoma antigen-specific cytotoxic T lymphocytes in vitro by stimulation with B7-expressing human melanoma cell lines. J Immunother. Mar. 1998;21(2):95-108.

Fulford et al., Basal-like grade III invasive ductal carcinoma of the breast: patterns of metastasis and long-term survival. Breast Cancer Res. 2007;9(1):R4.

Fulford et al., Specific morphological features predictive for the basal phenotype in grade 3 invasive ductal carcinoma of breast. Histopathology. Jul. 2006;49(1):22-34.

Gajewski et al., Costimulation with B7-1, IL-6, and IL-12 is sufficient for primary generation of murine antitumor cytolytic T lymphocytes in vitro. J Immunol. Jun. 1, 1995;154(11):5637-48.

Gilbert et al., A protein particle vaccine containing multiple malaria epitopes. Nat Biotechnol. Nov. 1997;15(12):1280-4.

Grigoriadis et al., Establishment of the epithelial-specific transcriptome of normal and malignant human breast cells based on MPSS and array expression data. Breast Cancer 2006;8(5):R56.

Gure et al., Cancer-testis genes are coordinately expressed and are markers of poor outcome in non-small cell lung cancer. Clin Cancer Res. Nov. 15, 2005;11(22):8055-62.

Hall, IL-12 at the crossroads. Science. Jun. 9, 1995;268(5216):1432-4.

Herold et al., Aromatase inhibitors for breast cancer: proven efficacy across the spectrum of disease. Clin Breast Cancer. Feb. 2008;8(1):50-64.

Hess et al., Pharmacogenomic predictor of sensitivity to preoperative chemotherapy with paclitaxel and fluorouracil, doxorubicin, and cyclophosphamide in breast cancer. J Clin Oncol. Sep. 10, 2006;24(26):4236-44. Epub Aug. 8, 2006.

Hoadley et al., EGFR associated expression profiles vary with breast tumor subtype. BMC Genomics. Jul. 31, 2007;8:258.

Hu et al., The molecular portraits of breast tumors are conserved across microarray platforms. BMC Genomics. Apr. 27, 2006;7:96.

Ivshina et al., Genetic reclassification of histologic grade delineates new clinical subtypes of breast cancer. Cancer Res. Nov. 1, 2006;66(21):10292-301.

Jäager et al., Recombinant vaccinia/fowlpox NY-ESO-1 vaccines induce both humoral and cellular NY-ESO-1-specific immune responses in cancer patients. Proc Natl Acad Sci U S A. Sep. 26, 2006;103(39):14453-8. Epub Sep. 19, 2006.

Jongeneel et al., An atlas of human gene expression from massively parallel signature sequencing (MPSS). Genome Res. Jul. 2005;15(7):1007-14.

Kim et al., Engineering of in vivo immune responses to DNA immunization via codelivery of costimulatory molecule genes. Nat Biotechnol. Jul. 1997;15(7):641-6.

Madarnas et al., Adjuvant/neoadjuvant trastuzumab therapy in women with HER-2/neu-overexpressing breast cancer: a systematic review. Cancer Treat Rev. Oct. 2008;34(6):539-57. Epub May 27, 2008.

Maraskovsky et al., NY-ESO-1 protein formulated in ISCOMATRIX adjuvant is a potent anticancer vaccine inducing both humoral and CD8+ T-cell-mediated immunity and protection against NY-ESO-1+ tumors. Clin Cancer Res. Apr. 15, 2004;10(8):2879-90.

Miller et al., An expression signature for p53 status in human breast cancer predicts mutation status, transcriptional effects, and patient survival. Proc Natl Acad Sci U S A. Sep. 20, 2005;102(38):13550-5. Epub Sep. 2, 2005.

Minn et al., Genes that mediate breast cancer metastasis to lung. Nature. Jul. 28, 2005;436(7050):518-24.

Mischo et al., Prospective study on the expression of cancer testis genes and antibody responses in 100 consecutive patients with primary breast cancer. Int J Cancer. Feb. 1, 2006;118(3):696-703.

Napoletano et al., MAGE-A and NY-ESO-1 expression in cervical cancer: prognostic factors and effects of chemotherapy. Am J Obstet Gynecol. Jan. 2008;198(1):99.e1-7.

Neve et al., A collection of breast cancer cell lines for the study of functionally distinct cancer subtypes. Cancer Cell. Dec. 2006;10(6):515-27.

Odunsi et al., Vaccination with an NY-ESO-1 peptide of HLA class I/II specificities induces integrated humoral and T cell responses in ovarian cancer. Proc Natl Acad Sci U S A. Jul. 31, 2007;104(31):12837-42. Epub Jul. 25, 2007.

Park et al., Trastuzumab treatment beyond brain progression in HER2-positive metastatic breast cancer. Ann Oncol. 2009; 20: 56-62. Epub Jul. 29, 2008.

Parra et al., The role of B7-1 and LFA-3 in costimulation of CD8+ T cells. J Immunol. Jan. 15, 1997;158(2):637-42.

Perou et al., Molecular portraits of human breast tumours. Nature. Aug. 17, 2000;406(6797):747-52.

Ponzone et al., Antihormones in prevention and treatment of breast cancer. Ann N Y Acad Sci. Nov. 2006;1089:143-58.

Quinn et al., Survival from cancer of the breast in women in England and Wales up to 2001. Br J Cancer. Sep. 23, 2008;99 Suppl 1:S53-5.

Rhodes et al., Oncomine: a cancer microarray database and integrated data-mining platform. Neoplasia. Jan.-Feb. 2004;6(1):1-6.

Ridge et al., A conditioned dendritic cell can be a temporal bridge between a CD4+ T-helper and a T-killer cell. Nature. Jun. 4, 1998;393(6684):474-8.

Rosenthal, Meta-analysis: a review. Psychosom Med. May-Jun. 1991;53(3):247-71. Review.

Scanlan et al., Cancer/testis antigens: an expanding family of targets for cancer immunotherapy. Immunol Rev. Oct. 2002;188:22-32.

Scanlan et al., The cancer/testis genes: review, standardization, and commentary. Cancer Immun. Jan. 23, 2004;23;4:1.

Schoenberger et al., T-cell help for cytotoxic T lymphocytes is mediated by CD40-CD40L interactions. Nature. Jun. 4, 1998;393(6684):480-3.

Simpson et al., Cancer/testis antigens, gametogenesis and cancer. Nat Rev Cancer. Aug. 2005;5(8):615-25.

So et al., Effect of a novel saponin adjuvant derived from Quillaja saponaria on the immune response to recombinant hepatitis B surface antigen. Mol Cells. Apr. 30, 1997;7(2):178-86.

Sørlie et al., Repeated observation of breast tumor subtypes in independent gene expression data sets. Proc Natl Acad Sci U S A. Jul. 8, 2003;100(14):8418-23. Epub Jun. 26, 2003.

Sotiriou et al., Gene expression profiling in breast cancer: understanding the molecular basis of histologic grade to improve prognosis. J Natl Cancer Inst. Feb. 15, 2006;98(4):262-72.

Sugita et al., NY-ESO-1 expression and immunogenicity in malignant and benign breast tumors. Cancer Res. Mar. 15, 2004;64(6):2199-204.

Tam et al., Incorporation of T and B epitopes of the circumsporozoite protein in a chemically defined synthetic vaccine against malaria. J Exp Med. Jan. 1, 1990;171(1):299-306.

Theurillat et al., NY-ESO-1 protein expression in primary breast carcinoma and metastases—correlation with CD8+ T-cell and CD79a+ plasmacytic/B-cell infiltration. Int J Cancer. Jun. 1, 2007;120(11):2411-7.

(56) References Cited

OTHER PUBLICATIONS

Thomson et al., Minimal epitopes expressed in a recombinant polyepitope protein are processed and presented to CD8+ cytotoxic T cells: implications for vaccine design. Proc Natl Acad Sci U S A. Jun. 20, 1995;92(13):5845-9.

Thomson et al., Recombinant polyepitope vaccines for the delivery of multiple CD8 cytotoxic T cell epitopes. J Immunol. Jul. 15, 1996;157(2):822-6.

Tinguely et al., A. MAGE-C1/CT-7 expression in plasma cell myeloma: sub-cellular localization impacts on clinical outcome. Cancer Sci. Apr. 2008;99(4):720-5. Epub Feb. 27, 2008.

Valmori et al., Vaccination with NY-ESO-1 protein and CpG in Montanide induces integrated antibody/Th1 responses and CD8 T cells through cross-priming. Proc Natl Acad Sci U S A. May 22, 2007;104(21):8947-52. Epub May 15, 2007.

Van Baren et al., Tumoral and immunologic response after vaccination of melanoma patients with an ALVAC virus encoding MAGE antigens recognized by T cells. J Clin Oncol. Dec. 10, 2005;23(35):9008-21. Epub Aug. 1, 2005.

Van De Vijver et al., A gene-expression signature as a predictor of survival in breast cancer. N Engl J Med. Dec. 19, 2002;347(25):1999-2009.

Velazquez et al., Expression of the cancer/testis antigen NY-ESO-1 in primary and metastatic malignant melanoma (MM)—correlation with prognostic factors. Cancer Immun. Jul. 12, 2007;7:11.

Wang et al., Gene-expression profiles to predict distant metastasis of lymph-node-negative primary breast cancer. Lancet. Feb. 19-25, 2005;365(9460):671-9.

Wang et al., Induction of autologous tumor-specific cytotoxic T-lymphocyte activity against a human renal carcinoma cell line by B7-1 (CD80) costimulation. J Immunother Emphasis Tumor Immunol. Jan. 1996;19(1):1-8.

Wendtner et al., Gene transfer of the costimulatory molecules B7-1 and B7-2 into human multiple myeloma cells by recombinant adeno-associated virus enhances the cytolytic T cell response. Gene Ther. Jul. 1997;4(7):726-35.

Zheng et al., B7-CTLA4 interaction enhances both production of antitumor cytotoxic T lymphocytes and resistance to tumor challenge. Proc Natl Acad Sci U S A. May 26, 1998;95(11):6284-9.

Scheel et al., Intradermal Immunization With a Novel mRNA Based Vaccination Technology Induces Strong T- and B-cell Responses in Phase I/ IIA Trials in Non-Small Cell Lung Cancer (NSCLC) and Prostate Carcinoma (PCA). J Immunother. 2011; 34(9):699. Abstract.

Sebastian et al., Phase Ib study evaluating a self-adjuvanted mRNA cancer vaccine (RNActive®) combined with local radiation as consolidation and maintenance treatment for patients with stage IV non-small cell lung cancer. BMC Cancer. 2014; 14:748.

* cited by examiner

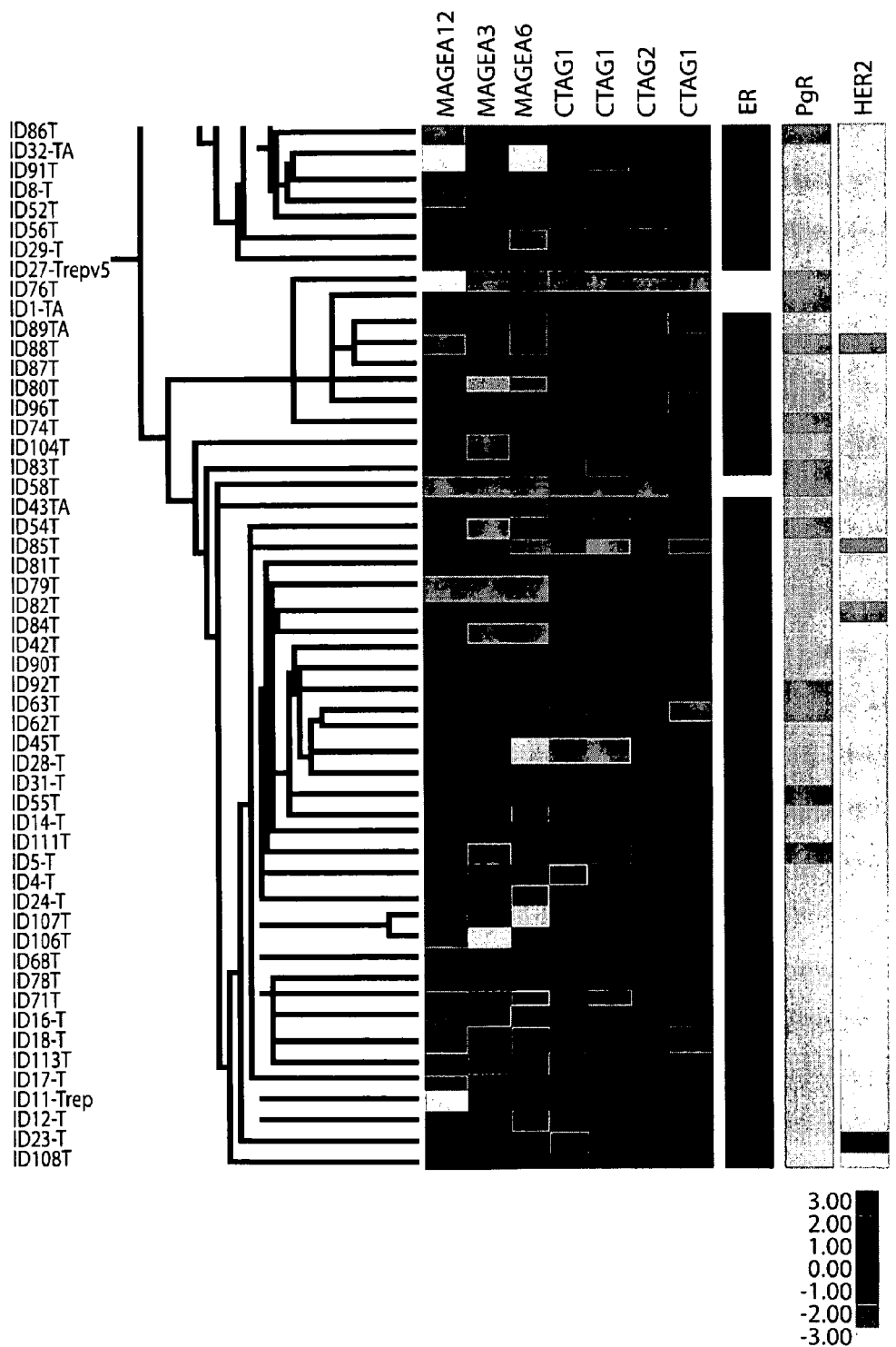

Doane et al, 2006

TARGETED TREATMENT FOR PATIENTS WITH ESTROGEN RECEPTOR NEGATIVE AND PROGESTERONE RECEPTOR NEGATIVE BREAST CANCERS

RELATED APPLICATIONS

This application is a national stage filing under 35 U.S.C. §371 of international application PCT/US2009/002483, filed Apr. 22, 2009, which was published under PCT Article 21(2) in English, and claims the benefit under 35 U.S.C. §119(e) of U.S. provisional application Ser. No. 61/125,521, filed on Apr. 25, 2008, the entire disclosures of each of which is incorporated herein by reference.

FIELD OF THE INVENTION

Treatments for estrogen receptor and progesterone receptor negative breast cancer or estrogen receptor, progesterone receptor and c-erbB2 negative (triple negative) breast cancer are provided.

BACKGROUND OF THE INVENTION

Cancer/testis (CT) antigens constitute a unique group of genes which are predominantly expressed in human germ line cells such as placenta and testis but become reactivated in various malignancies (Simpson et al., *Nature Rev* (2005) 5, 615-625). Most of these genes are located as multigene families on the X-chromosome and are often referred to as CT-X antigens (Simpson et al., *Nature Rev* (2005) 5, 615-625). So far their function has not been elucidated; however their involvement in chromosomal recombination, transcription as well as translation and signaling has been proposed (Simpson et al., *Nature Rev* (2005) 5, 615-625). Analogies have been drawn between their expression pattern during germ maturation and neoplastic transformation, thus suggesting their involvement in several steps of tumorigenesis (Simpson et al., *Nature Rev* (2005) 5, 615-625).

The expression of CT-X antigens varies greatly between tumor types. While bladder cancer, lung cancer, ovarian cancer, hepatocellular carcinoma and melanoma frequently express CT-X antigens, the abundance of these genes is less frequent in renal cancer, colon, and gastric cancers (Scanlan et al., *Cancer Immun* (2004) 4, 1). Moreover, their expression pattern is closely associated with advanced disease and poor outcome and might thus be of diagnostic and/or prognostic relevance (Gure et al., *Clin Cancer Res* (2005) 11, 8055-8062; Velazquez et al., *Cancer Immun* (2007) 7, 11; Andrade et al., *Cancer Immun* (2008) 8, 2; Tinguely et al., *Cancer Science* (2008); Napoletano et al., *Am J of Obstet Gyn* (2008) 198, 99 e91-97. Due to their highly restricted expression in malignant tissues, their tumor associated peptides provide promising targets for anticancer immunotherapy (Scanlan et al., *Immunol Rev* (2002) 188, 22-32). Indeed, clinical trials evaluating the role of two CT antigens, namely MAGE-A3 and NY-ESO-1, as targets for specific immunotherapy have already been initiated in a number of different malignancies (Bender et al., *Cancer Immunol* (2007) 7, 16; Atanackovic et al., *PNAS* (2008) 105, 1650-1655; Jager et al., *PNAS* (2006) 103, 14453-14458; van Baren et al., *J Clin Oncol* (2005) 23, 9008-9021; Valmori et al., *PNAS* (2007) 104, 8947-8952; Odunsi et al., *PNAS* (2007) 104, 12837-12842; Davis et al., *PNAS* (2004) 101, 10697-10702 (9-15).

In breast-cancer most known tumour antigens can be found in normal tissues with elevated and or mutated expression in tumors cells. Some of these antigens such as MUC1, CEA, carbohydrate antigens and HER-2/ERBB2 have already been used to construct vaccines for the treatment of breast cancer (Curigliano et al., *Breast* (Edinburgh, Scotland) (2007) 16 Supp. 2, S20-26). So far targeted immunotherapy treatment has been successful with the monoclonal antibody trastuzumab (Herceptin®) against HER-2/ERBB2 receptors and it has been shown to be most effective for a subpopulation of breast cancers with HER2/ERBB2 over-expression. While other subtypes such as ER-positive (ER$^+$) breast tumour patients benefit from endocrine and or combinatorial therapy, targeted therapy for a distinctive group of ER-negative (ER$^-$) is still in its infancy. Recent studies have shown good responses for some ER-negative breast cancers with EGFR overexpression when treated with carboplatin in combination monoclonal antibodies (cetuximab) (Hoadley et al., *BMC Genomics* (2007) 8, 258).

Current clinical management of breast cancer—early detection, surgery and cytotoxic drug regimens often in the adjuvant setting—has resulted in significant gains in disease free and overall survival in recent times (Quinn et al., *Br J Cancer* (2008) 99 Sup. 1, S53-55). Some additional advances have been achieved through the use of targeted forms of therapy such as Tamoxifen and aromatase inhibitors for those breast cancers possessing estrogen receptors (Herold et al., *Clin Breast Cancer* (2008) 8, 50-64; Ponzone et al., *Ann NY Acad Sciences* (2006) 1089, 143-158). Trastuzumab (Herceptin®), a humanized monoclonal antibody against the extracellular domain of HER2, has been shown recently to benefit patients with HER2-positive primary and metastatic disease (Madarnas et al., *Cancer Tr Rev* (2008) 34, 539-557; Park et al., *Ann Oncol* (2008)).

SUMMARY OF THE INVENTION

There remains a need to develop further tumor specific targets particularly for those tumors that lack steroid receptors and do not have amplification of HER2. To date, only a few studies have looked at the expression patterns of CT-X antigens in breast cancers and their association with higher grade lesions was inferred (Theurillat et al., *Intern J Cancer* (2007) 120, 2411-2417; Bandic et al., *Croatian Med J* (2007) 47, 32-41; Mischo et al., *Intern J Cancer* (2006) 118, 696-703; Sugita et al., *Cancer Res* (2004) 64, 2199-2204). However the lesions studied were restricted in number and were concerned primarily with NY-ESO-1 expression.

To date, immunotherapeutic regimens for breast cancer have been used mainly in end stage disease and have generally employed antigens expressed in normal tissues with elevated expression or expression of mutated forms in tumor cells. Included in this category are antigens such as MUC1, CEA and the carbohydrate antigens (Chin et al., *Cancer Cell* (2006) 10, 529-541). By contrast current thinking places the role of immunotherapy as being most likely to be effective when patients only have minimal residual disease after initial treatment. CT-X antigens through their restricted distribution in the testis and cancer cells offer a more specific opportunity for vaccine development and therapy. Currently vaccines comprising members of the MAGE and ESO families are in clinical trials in patients with melanoma and lung cancer where such antigens are frequently expressed (Bender et al., *Cancer Immunol* (2007) 7, 16; Atanackovic et al., *PNAS* (2008) 105, 1650-1655; Jager et al., *PNAS* (2006) 103, 14453-14458; van Baren et al., *J Clin Oncol* (2005) 23, 9008-9021; Valmori et al., *PNAS* (2007) 104, 8947-8952; Odunsi et al., *PNAS* (2007) 104, 12837-12842; Davis et al., *PNAS* (2004) 101, 10697-10702; Theurillat et al., *Intern J Cancer* (2007) 120, 2411-2417).

Thus, the present study has carried out a comprehensive gene expression analysis of CT-X antigens in primary breast cancer and correlated the findings with a series of clinicopathological factors. Our results pointed to a restricted expression of CT antigens including NY-ESO-1 and some members of the MAGEA family in a subset of ER/PR negative and p53-mutated primary breast tumors. CT-X-based immunotherapy strategies may, therefore, also be relevant for some patients with ER/PR negative and p53-mutated breast cancers as has already been noted for other tumor systems.

According to one aspect of the invention, methods for treating breast cancer are provided. The methods include administering to a subject having a breast tumor that is estrogen receptor and progesterone receptor negative (ER/PR-negative) an amount of one or more cancer-testis (CT) antigen proteins or one or more immunogenic peptides of CT antigen proteins, wherein the amount is effective to induce or increase an immune response against the one or more protein(s) and/or peptide(s).

In some embodiments, the breast tumor also is c-erbB2 negative. In certain embodiments, the breast tumor also has p53 mutations.

In some embodiments, the CT antigen protein or peptide is one or more of a CTAG (NY-ESO-1/LAGE) protein, a MAGE protein, a SSX protein, a GAGE protein, a SPANX protein, a XAGE protein, a CSAG protein, CXorf48 protein, or a CT45 protein or one or more immunogenic peptides of CTAG (NY-ESO-1/LAGE), MAGE, SSX, GAGE, SPANX, XAGE, CSAG, CXorf48, or CT45. In some embodiments, the protein or peptide administered is a CTAG1 protein or peptide, such as a NY-ESO-1 or LAGE protein or peptide; a MAGE protein or peptide, such as a MAGE-A3 protein or peptide; a SSX protein or peptide; a CT45 protein or peptide; or a GAGE, SPANX, XAGE, CSAG, or CXorf48 protein or peptide.

In some embodiments, the methods also include testing a biological sample of the subject during and/or after therapy for the presence of tumor cells. In certain embodiments, the biological sample is a breast tissue biopsy, blood or bone marrow. In some embodiments, the presence of tumor cells is determined by immunohistochemistry and/or analysis of gene expression. In certain embodiments, the analysis of gene expression is performed using polymerase chain reaction or microarray analysis.

In some embodiments, the CT antigen or peptide is administered as part of a composition, and optionally the composition also includes an adjuvant. In certain embodiments, the adjuvant is selected from MPL, QS21, or a water-in-oil emulsion prepared from squalene and/or tocopherol.

In some embodiments, the methods also include the step of administering one or more additional agents stimulating and/or potentiating the immune response in the subject.

In some embodiments of the foregoing methods, two or more CT antigens or immunogenic peptides or fragments thereof are joined together to form a polytope.

According to another aspect of the invention, methods for treating breast cancer are provided. The methods include determining the expression of estrogen receptor (ER) and progesterone receptor (PR) in cells of a breast tumor obtained from a subject, and administering to a subject having a breast tumor that is ER/PR-negative an amount of one or more cancer-testis (CT) antigen proteins or one or more immunogenic peptides of CT antigen proteins, wherein the amount is effective to induce or increase an immune response against the one or more protein(s) and/or peptide(s).

In some embodiments, the methods also include determining the expression of c-erbB2 in cells of the breast tumor. In certain embodiments, the methods also include determining the mutation status of p53 in cells of the breast tumor.

In some embodiments, the CT antigen protein or peptide is one or more of a CTAG (NY-ESO-1/LAGE) protein, a MAGE protein, a SSX protein, a GAGE protein, a SPANX protein, a XAGE protein, a CSAG protein, CXorf48 protein, or a CT45 protein or one or more immunogenic peptides of CTAG (NY-ESO-1/LAGE), MAGE, SSX, GAGE, SPANX, XAGE, CSAG, CXorf48, or CT45. In some embodiments, the protein or peptide administered is a CTAG1 protein or peptide, such as a NY-ESO-1 or LAGE protein or peptide; a MAGE protein or peptide, such as a MAGE-A3 protein or peptide; a SSX protein or peptide; a CT45 protein or peptide; or a GAGE, SPANX, XAGE, CSAG, or CXorf48 protein or peptide.

In some embodiments, the methods also include testing a biological sample of the subject during and/or after therapy for the presence of tumor cells. In certain embodiments, the biological sample is a breast tissue biopsy, blood or bone marrow. In some embodiments, the presence of tumor cells is determined by immunohistochemistry and/or analysis of gene expression. In certain embodiments, the analysis of gene expression is performed using polymerase chain reaction or microarray analysis.

In some embodiments, the CT antigen or peptide is administered as part of a composition, and optionally the composition also includes an adjuvant. In certain embodiments, the adjuvant is selected from MPL, QS21, or a water-in-oil emulsion prepared from squalene and/or tocopherol.

In some embodiments, the methods also include the step of administering one or more additional agents stimulating and/or potentiating the immune response in the subject.

In some embodiments of the foregoing methods, two or more CT antigens or immunogenic peptides or fragments thereof are joined together to form a polytope.

According to yet another aspect of the invention, methods for determining the suitability of a subject for immunotherapy of breast cancer are provided. The methods include determining the expression of estrogen receptor (ER) and progesterone receptor (PR) in cells of a breast tumor of a subject, wherein a subject who has a breast tumor that is ER-negative and PR-negative is a subject that is suited for immunotherapy that comprises administering to the subject an amount of one or more cancer-testis (CT) antigen proteins or one or more immunogenic peptides of CT antigen proteins; wherein the amount is effective to induce or increase an immune response against the one or more protein(s) and/or peptide(s).

In some embodiments, the methods also include determining the expression of c-erbB2 in cells of the breast tumor. In certain embodiments, the methods also include determining the mutation status of p53 in cells of the breast tumor.

In some embodiments, the CT antigen protein or peptide is one or more of a CTAG (NY-ESO-1/LAGE) protein, a MAGE protein, a SSX protein, a GAGE protein, a SPANX protein, a XAGE protein, a CSAG protein, CXorf48 protein, or a CT45 protein or one or more immunogenic peptides of CTAG (NY-ESO-1/LAGE), MAGE, SSX, GAGE, SPANX, XAGE, CSAG, CXorf48, or CT45. In some embodiments, the protein or peptide administered is a CTAG1 protein or peptide, such as a NY-ESO-1 or LAGE protein or peptide; a MAGE protein or peptide, such as a MAGE-A3 protein or peptide; a SSX protein or peptide; a CT45 protein or peptide; or a GAGE, SPANX, XAGE, CSAG, or CXorf48 protein or peptide.

In some embodiments, the methods also include testing a biological sample of the subject during and/or after therapy for the presence of tumor cells. In certain embodiments, the biological sample is a breast tissue biopsy, blood or bone marrow. In some embodiments, the presence of tumor cells is determined by immunohistochemistry and/or analysis of gene expression. In certain embodiments, the analysis of gene expression is performed using polymerase chain reaction or microarray analysis.

In some embodiments, the CT antigen or peptide is administered as part of a composition, and optionally the composition also includes an adjuvant. In certain embodiments, the adjuvant is selected from MPL, QS21, or a water-in-oil emulsion prepared from squalene and/or tocopherol.

In some embodiments, the methods also include the step of administering one or more additional agents stimulating and/or potentiating the immune response in the subject.

In some embodiments of the foregoing methods, two or more CT antigens or immunogenic peptides or fragments thereof are joined together to form a polytope.

In some embodiments of any of the foregoing methods, the expression of ER, PR and/or c-erbB2 is determined by immunohistochemistry and/or analysis of gene expression. In certain embodiments, the analysis of gene expression is performed using polymerase chain reaction or microarray analysis.

In some embodiments of any of the foregoing methods, the mutation status of p53 in cells of the breast tumor is determined using polymerase chain reaction, nucleic acid sequencing or microarray analysis.

According to one aspect of the invention, methods and uses for treating breast cancer are provided. The methods and uses include administering to a subject having a breast tumor that is estrogen receptor and progesterone receptor negative (ER/PR-negative) an amount of one or more cancer-testis (CT) antigen proteins or one or more immunogenic peptides of CT antigen proteins. The amount is effective to induce or increase an immune response against the one or more protein(s) and/or peptide(s).

"One or more" for the purpose of this application includes, but is not limited to, two or more, three or more, four or more, five or more, six or more, seven or more, eight or more, nine or more, and ten or more.

According to another aspect of the invention, additional methods and uses for treating breast cancer are provided. The methods and uses include determining the expression of estrogen receptor (ER) and progesterone receptor (PR) in cells of a breast tumor obtained from a subject, and administering to a subject having a breast tumor that is ER/PR-negative an amount of one or more cancer-testis (CT) antigen proteins or one or more immunogenic peptides of CT antigen proteins. The amount is effective to induce or increase an immune response against the one or more protein(s) and/or peptide(s).

According to another aspect of the invention, methods and uses for determining the suitability of a subject for immunotherapy of breast cancer are provided. The methods include determining the expression of estrogen receptor (ER) and progesterone receptor (PR) in cells of a breast tumor of a subject. A subject who has a breast tumor that is ER-negative and PR-negative is a subject that is suited for immunotherapy that comprises administering to the subject an amount of one or more cancer-testis (CT) antigen proteins or one or more immunogenic peptides of CT antigen proteins, wherein the amount is effective to induce or increase an immune response against the one or more protein(s) and/or peptide(s).

In some embodiments of the foregoing methods and uses, the breast tumor also is c-erbB2 negative in addition to being ER/PR-negative. In further embodiments of the foregoing methods, the breast tumor also has p53 mutations.

In some embodiments of the foregoing methods and uses, the expression of ER, PR and/or c-erbB2 is determined by immunohistochemistry and/or analysis of gene expression. The analysis of gene expression in certain embodiments is performed using polymerase chain reaction or microarray analysis.

In other embodiments of the foregoing methods and uses, the mutation status of p53 in cells of the breast tumor is determined using polymerase chain reaction, nucleic acid sequencing or microarray analysis.

In some embodiments of the foregoing methods and uses, the CT antigen protein or peptide is one or more of a CTAG protein, a MAGE protein, a SSX protein or a CT45 protein or one or more immunogenic peptides of CTAG, MAGE, SSX or CT45. The CTAG protein or peptide in some embodiments is a CTAG1 protein or peptide, such as a NY-ESO-1 or LAGE protein or peptide. In other embodiments of the foregoing methods and uses, the MAGE protein or peptide is a MAGE-A3 protein or peptide. In further embodiments of the foregoing methods and uses, the protein or peptide administered is a SSX protein or peptide or a CT45 protein or peptide.

The foregoing methods also can include testing a biological sample of the subject during and/or after therapy for the presence of tumor cells. In some embodiments, the biological sample is blood or bone marrow.

The presence of tumor cells in certain embodiments of the foregoing methods and uses is determined by immunohistochemistry and/or analysis of gene expression. Analysis of gene expression is performed using polymerase chain reaction or microarray analysis in some embodiments of the foregoing methods and uses.

In some embodiments, uses of one or more cancer-testis (CT) antigen proteins or one or more immunogenic peptides of CT antigen proteins are provided in the manufacture of a medicament for the treatment of ER/PR-negative or triple negative breast cancer.

In some embodiments, uses of one or more cancer-testis (CT) antigen proteins or one or more immunogenic peptides of CT antigen proteins are provided in the manufacture of a medicament for increasing an immune response against the one or more protein(s) and/or peptide(s) in a subject having ER/PR-negative or triple negative breast cancer.

In some embodiments, uses of one or more cancer-testis (CT) antigen proteins or one or more immunogenic peptides of CT antigen proteins are provided in the manufacture of a medicament for immunotherapy of ER/PR-negative or triple negative breast cancer.

Other aspects of the invention and embodiments will be apparent from the drawings and further description provided herein.

DETAILED DESCRIPTION OF THE INVENTION

Figure 1A:
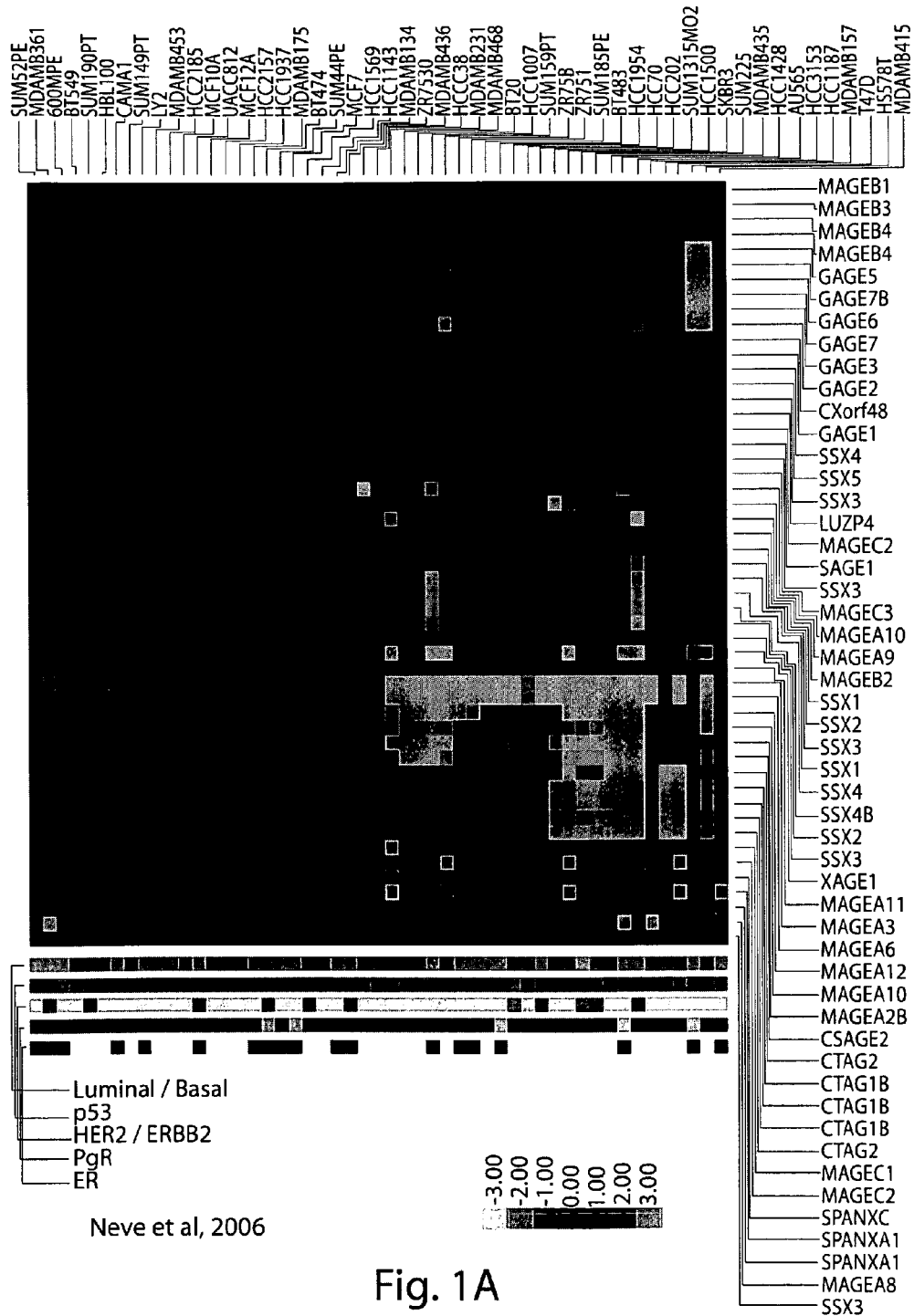
FIG. 1A-FIG. 1D correspond to expression profiles of CT-X antigens of (A) Neve et al. "breast cancer cell lines," *Cancer Cell* (2006) 10, 515-527); (B) Chin et al., *Cancer Cell* (2006) 10, 529-541, (C) Hu et al., *BMC Genomics* (2006) 7, 96; and (D) Doane et al., "primary breast cancers," *Oncogene* (2006) 25, 3994-4008). CT-X antigens are shown on the right. The ER-status is indicated for each heatmap with a bar labeled "ER." Light gray indicates ER$^-$ and dark gray indicates ER$^+$ breast tumors. Expression levels are pseudocolored; red indicating transcript levels above the median for that probe set across all samples and green below the median.

It has been discovered that expression of certain cancer-testis (CT) antigens, e.g., NY-ESO-1 and some members of the MAGEA family, is restricted to a subset of estrogen receptor and progesterone receptor negative (ER/PR negative) breast tumors. Patients with ER/PR negative breast tumors have a bad prognosis. Moreover, there is no rational targeted therapy for this group of patients. Some ER/PR negative tumors also are c-erbB2-negative, a subset of ER/PR negative tumors known as "triple negative" breast tumors. Triple negative tumors are aggressive tumors. In addition, some of the breast tumors contain p53 mutations.

Patients having ER/PR-negative breast cancer today only get adjuvant chemotherapy; in accordance with the invention disclosed herein, adjuvant immunotherapy using CT antigens can be added to existing treatment regimes. The recognition that ER/PR-negative tumors express CT antigens provides the ability to diagnose such tumors and to treat a certain population of subjects having such tumors.

In some aspects of the invention, methods for treating breast cancer are provided that include administering to a subject having an ER/PR-negative breast tumor an amount of one or more cancer-testis (CT) antigen proteins or one or more immunogenic peptides of CT antigen proteins, wherein the amount is effective to induce or increase an immune response against the one or more protein(s) and/or peptide(s). In some embodiments, the tumors also are characterized as being c-erbB2 negative and/or have mutations in the p53 gene. C-erbB2 is also known as HER2 and neu, among other synonyms. Methods for administering proteins and peptides for immunotherapy, including preparation and formulation of the proteins and peptides as medicaments, are well known in the art. Reference may be made to various clinical trials of CT antigen immunotherapy that have been conducted, as well as more general knowledge in the art that is embodied in texts such as Goodman and Gilman's The Pharmacological Basis of Therapeutics, Goodman and Gilman's Manual of Pharmacology and Therapeutics and Remington's Pharmaceutical Sciences.

Cancer-testis antigens are well known in the art. In some embodiments, certain CT antigens are used in the methods described herein, such as CTAG proteins, MAGE proteins, SSX proteins and CT45 proteins. The methods described herein also can use immunogenic peptides of CT antigens. Such CT antigens and immunogenic peptides thereof are well known in the art, having been described in literature articles, patents and patent applications, particularly those of the Ludwig Institute for Cancer Research.

CTAG proteins include CTAG1 and CTAG2 proteins. CTAG1 proteins include NY-ESO-1 and LAGE-2. CTAG2 proteins include ESO2, LAGE-1, LAGE-2b, CAMEL, MGC138724 and MGC3803. Several MAGE proteins are known, including MAGE-A1, A3, A4, A5, A6 and A9 proteins. Several SSX proteins are known, including SSX1, SSX2, SSX3 and SSX5.

One or more cancer testis (CT) antigens or one or more immunogenic peptide of CT antigen proteins may be administered as part of a composition, preparation and/or formulation. In certain embodiments, these compositions, preparations and/or formulations are administered with one or more adjuvants to induce an immune response or to increase an immune response.

An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella Minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol Cells* (1997) 7:178-186); ISCOMATRIX adjuvant, a cage-like structure composed of saponin, phospholipid, and cholesterol (see, e.g., Maraskovsky et al., *Clin. Cancer Res.* (2004) 10:2879-2890); incomplete Freund's adjuvant; complete Freund's adjuvant; montanide; and various water-in-oil emulsions prepared from biodegradable oils such as squalene and/or tocopherol.

In certain embodiments, the CT antigens and immunogenic peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. In certain embodiments, the CT antigens and immunogenic peptides are administered in water-in-oil emulsions. Other adjuvants are known in the art and can be used in the invention (see, e.g., Goding,

*Monoclonal Antibodies: Principles and Practice*, (1986) 2nd Ed.). Methods for the preparation of mixtures or emulsions of antigens and peptide and adjuvant are well known to those of skill in the art.

Other agents which stimulate the immune response of a subject may also be administered to the subject. For example, cytokines are also useful in vaccination protocols as a result of their lymphocyte regulatory properties. Many cytokines useful for such purposes will be known to one of ordinary skill in the art, including interleukin-12 (IL-12) which has been shown to enhance the protective effects of vaccines (see, e.g., *Science* (1995) 268: 1432-1434), GM-CSF and IL-18. Thus cytokines can be administered in conjunction with CT antigens and adjuvants to increase the immune response to the CT antigens.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *PNAS* (1998) 95:6284-6289).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J Immunol* (1995) 154:5637-5648). Tumor cell transfection with B7 has been discussed in relation to in vitro CTL expansion for adoptive transfer immunotherapy by Wang et al. (*J. Immunother* (1996) 19:1-8). Other delivery mechanisms for the B7 molecule would include nucleic acid (naked DNA) immunization (Kim et al., *Nature Biotechnol* (1997) 15:7:641-646) and recombinant viruses such as adeno and pox (Wendtner et al., *Gene Ther* (1997) 4:726-735). These systems are all amenable to the construction and use of expression cassettes for the coexpression of B7 with other molecules of choice such as the CT antigens or fragment(s) of antigens discussed herein (including polytopes). These delivery systems can be used for induction of the appropriate molecules in vitro and for in vivo vaccination situations. The use of anti-CD28 antibodies to directly stimulate T cells in vitro and in vivo may also be used.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J Immunol*, (1997) 158:637-642; Fenton et al., *J. Immunother*, (1998) 21:95-108).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function may also require T helper (Th) cell help through the interaction between the Th cell CD40L (CD40 ligand) molecule and the CD40 molecule expressed by DCs (Ridge et al., *Nature* (1998) 393:474; Bennett et al., *Nature* (1998) 393:478; Schoenberger et al., *Nature* (1998) 393:480). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

One or more cancer testis (CT) antigens or one or more immunogenic peptide of CT antigen proteins, described herein, may be administered individually, or they may be presented as a series of epitopes, known as "polytopes." The epitopes can be arranged in sequential or overlapping fashion (see, e.g., Thomson et al., *PNAS* (1995) 92:5845-5849; Gilbert et al., *Nature Biotechnol* (1997) 15:1280-1284), with or without the natural flanking sequences, and can be separated by unrelated linker sequences, if desired. The polytope is processed to generated individual epitopes, which are recognized by the immune system for generation of immune responses.

For example, multiple CT antigens and immunogenic peptides thereof, disclosed herein, that are presented by MHC molecules and recognized by CTL or T helper lymphocytes, can be combined, e.g., by preparation of hybrid nucleic acids or polypeptides, to form "polytopes." The two or more peptides (or nucleic acids encoding the peptides) can be selected from the CT antigens described herein, or they can include one or more peptides of previously known cancer associated antigens. Exemplary cancer associated peptide antigens that can be administered to induce or enhance an immune response are derived from tumor associated genes and encoded proteins including MAGE-1, MAGE-2, MAGE-3, MAGE-4, MAGE-5, MAGE-6, MAGE-7, MAGE-8, MAGE-9, MAGE-10, MAGE-11, GAGE-1, GAGE-2, GAGE-3, GAGE-4, GAGE-5, GAGE-6, BAGE-1, RAGE-1, LB33/MUM-1, PRAME, NAG, MAGE-Xp2, MAGE-Xp3, MAGE-Xp4, tyrosinase, brain glycogen phosphorylase, Melan-A, and MAGE-C1. See, for example, PCT application publication no. WO96/10577. Other examples will be known to one of ordinary skill in the art (for example, see Simpson et al., Nat Rev Cancer. 2005; 5(8):615-625; Coulie, *Stem Cells* (1995) 13:393-403), and can be used in the invention in a like manner as those disclosed herein. One of ordinary skill in the art can prepare polypeptides comprising one or more CT antigens or antigenic peptides and one or more of the foregoing cancer associated peptides, or nucleic acids encoding such polypeptides, according to standard procedures of molecular biology.

Polytopes are groups of two or more potentially immunogenic or immune response stimulating peptides which can be joined together in various arrangements (e.g., concatenated, overlapping). The peptides can be joined together directly or via the use of flanking sequences to form polytopes, and the use of polytopes as vaccines is well known in the art (see, e.g., Thomson et al., *PNAS* (1995) 92(13):5845-5849; Gilbert et al., *Nature Biotechnol* (1997) 15(12):1280-1284; Thomson et al., *J Immunol* (1996) 157(2):822-826; Tam et al., *J Exp Med* (1990) 171(1):299-306). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing a subset of tumor rejection antigens expressed in a particular patient. Polytopes also can be prepared to reflect a broader spectrum of tumor rejection antigens known to be expressed by a particular tumor type.

Polytopes can be introduced to a patient in need of such treatment as polypeptide structures, or via the use of nucleic acid delivery systems known in the art (see, e.g., Allsopp et al., *Eur J Immunol* (1996) 26(8):1951-1959). Adenovirus, pox virus, Ty-virus like particles, adeno-associated virus, plasmids, bacteria, etc. can be used in such delivery.

Polytopes (or nucleic acid encoding the polytope) can be administered in a standard immunization protocol, e.g., to animals, to test the effectiveness of the polytope in stimulating, enhancing and/or provoking an immune response. Likewise, polytope delivery systems can be tested in mouse models to determine efficacy of the delivery system. The systems also can be tested in human clinical trials.

In certain embodiments, the polytopes may be administered to a subject in need thereof to treat a disease. In a preferred embodiment, the subject is a human and the disease is breast cancer, such as estrogen receptor and progesterone receptor (ER/PR)-negative breast cancer or "triple negative" breast cancer (ER, PR, and c-erbB2-negative tumors).

In certain embodiments, variants of CT antigens are provided. As used herein, a "variant" of a CT antigen polypeptide is a polypeptide which contains one or more modifications to the primary amino acid sequence of a CT antigen polypeptide. Modifications which create a CT antigen variant can be made to a CT antigen polypeptide 1) to reduce or eliminate an activity of a CT antigen polypeptide; 2) to enhance a property of a CT antigen polypeptide, such as protein stability in an expression system or the stability of protein-protein binding; 3) to provide a novel activity or property to a CT antigen polypeptide, such as addition of an antigenic epitope or addition of a detectable moiety; or 4) to provide equivalent or better binding to an HLA molecule. Modifications to a CT antigen polypeptide are typically made to the nucleic acid which encodes the CT antigen polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the CT antigen amino acid sequence. One of skill in the art will be familiar with methods for predicting the effect on protein conformation of a change in protein sequence, and can thus "design" a variant CT antigen polypeptide according to known methods. One example of such a method is described by Dahiyat and Mayo in *Science* (1997) 278:82-87, whereby proteins can be designed de novo. The method can be applied to a known protein to vary a only a portion of the polypeptide sequence. By applying the computational methods of Dahiyat and Mayo, specific variants of a CT antigen polypeptide can be proposed and tested to determine whether the variant retains a desired conformation.

The treatment methods and uses for treatment described herein can also include testing a subject for the presence of tumor cells. For example, a biological sample can be obtained from the subject, such as a breast biopsy sample, blood or bone marrow, before during and/or after therapy. The sample can be tested for the presence of tumor cells, using methods well known in the art. Such methods include, but are not limited to, immunological based methods such as immunohistochemistry and analysis of gene expression. More than one such method can be used in combination if desired. Analysis of gene expression can be performed using methods well known in the art, such as polymerase chain reaction or microarray analysis. The presence of tumor cells can be determined prior to therapy as a baseline for comparison with additional determinations made during or after therapy. A reduction in the presence of tumor cells in the subject can be used as an indication that the CT antigen immunotherapy is effective.

In some embodiments of the treatment methods, the subject is first tested to determine or confirm that the breast tumor of the subject is ER/PR-negative or triple negative (ER, PR, and c-erbB2-negative). In those embodiments, the method includes determining the expression of estrogen receptor (ER) and progesterone receptor (PR) (and optionally c-erbB2) in cells of a breast tumor obtained from a subject, and administering to a subject having a breast tumor that is ER/PR-negative or triple negative an amount of one or more cancer-testis (CT) antigen proteins or one or more immunogenic peptides of CT antigen proteins, wherein the amount is effective to induce or increase an immune response against the one or more protein(s) and/or peptide(s).

In other embodiments, the testing can be conducted simultaneously with therapy or after therapy. In such cases the CT antigen immunotherapy may be started prior to testing or prior to knowing the results of the testing for ER/PR (and optionally c-erbB2) status.

The testing aspects described above also can be applied to c-erbB2 expression status and p53 mutation status of the tumor of the patient.

The expression of ER, PR and/or c-erbB2 may be determined by any of the methods known in the art, such as immunohistochemistry and/or analysis of gene expression. Analysis of gene expression can be performed using any of the methods known in the art, of which two are polymerase chain reaction and microarray analysis. The mutation status of p53 in cells of the breast tumor can be determined using any method known in the art, such as polymerase chain reaction, nucleic acid sequencing or microarray analysis.

The invention also provides for determining the suitability of a subject for immunotherapy of breast cancer independent of treatment. In such methods, the expression of estrogen receptor (ER) and progesterone receptor (PR) in cells of a breast tumor of a subject is determined as described herein. A subject who has a breast tumor that is ER-negative and PR-negative is a subject that is suited for CT antigen immunotherapy. The tumor of the subject also can be tested for c-erbB2 expression status and p53 mutation status.

Various standard breast cancer therapeutic methods and chemotherapeutic compounds are well known in the art and can be used in combination with CT antigen immunotherapy in the selected patient population as described herein. A listing of certain chemotherapeutic compounds and other aspects of breast cancer therapy and care can be found, for example, in US published application 2006/0275305, the contents of which relating to chemotherapeutic compounds and other aspects of breast cancer therapy are incorporated herein by reference.

The treatment of breast cancer is determined by many factors, such as tumor stage, tumor type, tumor characteristics, the patient's general health, and medical conditions that may influence treatment. Treatment typically involves some form of surgery to remove as much of the cancer as possible.

A number of surgical procedures are used to treat breast cancer. Common surgeries for breast cancer include lumpectomy, partial mastectomy, total mastectomy, modified radical mastectomy, radical mastectomy, skin-sparing mastectomy, subcutaneous mastectomy, axillary dissection and sentinel lymph node biopsy.

Lumpectomy removes the cancer, a surrounding border of cancer-free tissue, and the nearby lymph nodes.

Partial mastectomy is a term for surgery in which part of the breast is removed. The axillary (underarm) lymph nodes are removed through the original incision or via a separate incision in the armpit itself. Total mastectomy removes the entire breast, without removing the underarm lymph nodes or muscular tissue beneath the breast. Modified radical mastectomy (also known as Patey mastectomy) removes the entire breast and some of the underarm lymph nodes. Radical mastectomy (also known as the Halsted procedure) is a very invasive surgical procedure that involves extensive removal of chest tissue. In addition to the entire breast and axillary lymph nodes, this operation removes the chest muscles under the breast and the surrounding skin. Radical mastectomy is rarely performed, because modified radical mastectomy has proven to be an equally effective technique with less disfigurement. Skin-sparing mastectomy is a variation of total mastectomy in which the breast tissue is removed through a tiny circular incision that is made around the nipple.

Axillary dissection is used to determine whether or not cancer has spread to the lymph nodes under the arm. During this procedure, a section of underarm fat and adjoining lymph nodes are removed for histopathological analysis. Axillary dissection may be conducted as part of a modified radical mastectomy or as a separate underarm incision that is made during lumpectomy.

Sentinel lymph node biopsy uses a radioactive substance to target the lymph nodes that are likely to be affected by breast cancer. A radioactive tracer is injected into the tumor and is eventually carried by the lymph to the first 'sentinel' node in the tumor's lymphatic pathway. If the cancer has spread, this node is most likely to contain cancer cells and is biopsied for analysis of the presence of malignant cells.

In addition to surgery, breast cancer treatment may include adjuvant therapy such as radiation therapy, chemotherapy, and/or hormone therapy. Other treatment options that may be used for aggressive or late-stage breast cancers are high-dose chemotherapy with bone marrow transplantation.

Radiation therapy, or radiotherapy, uses high-energy rays (x-rays, gamma rays) to destroy cancer cells. Radiation therapy is delivered by means of linear accelerators that generate x-rays and electrons and direct them as an external beam. Another device, the cobalt machine, gives off gamma rays from a radioactive source of cobalt.

Radiation therapy usually is given after breast-conserving surgery, that is, after lumpectomy or partial mastectomy for early-stage cancers. Radiation therapy helps to eliminate any cancer cells that may remain in the breast and is used to prevent local recurrence and to avoid the need for mastectomy.

An internal boost of radiotherapy may be used as an alternative treatment. During this procedure, a radioactive isotope like iridium (Ir192) is implanted into the breast cancer by means of hollow plastic tubes. The implants remain in place for about 2 days, after which they are removed. In some cases (for example, cancers deep within the breast), the internal boost may be given during the removal of the tumor, before the surgical incision is closed.

Lymph nodes may be treated by external beam radiation under certain circumstances. For example, if breast cancer has spread to the axillary lymph nodes, then the supraclavicular lymph nodes (above the collarbone) are at high risk and may need to be irradiated. Also, if breast cancer is located near the middle of the body, then the internal mammary lymph nodes may require radiation therapy.

Chemotherapy is the use of anticancer drugs to destroy cancer cells. Chemotherapy is given as an adjuvant therapy to reduce the chance of cancer recurring after surgery, radiation therapy, or both. Adjuvant chemotherapy, like hormone therapy, usually is started about four weeks after surgery. Neoadjuvant chemotherapy is given before surgery to shrink the breast tumor and make it easier to remove. Specific schedules are followed during chemotherapy, so that periods of treatment are accompanied by periods of recovery. Most treatment schedules are completed within three to six months.

Examples of drugs used for breast cancer chemotherapy include: Cytoxan®(Cyclophosphamide), Methotrexate, 5-Fluorouracil (5-FU), Adriamycin® (Doxorubicin), Prednisone, Nolvadex® (Tamoxifen), Taxol® (Paclitaxel), Leucovorin, Oncovin® (Vincristine), Thioplex® (Thiotepa), Arimidex® (Anastrozole), Taxotere® (Docetaxel), Navelbine®, (Vinorelbine tartrate), Gemzar® (Gemcitabine).

Examples of combination chemotherapy include the following: CMF (cyclophosphamide, methotrexate, and 5-fluorouracil); classic CMF (oral cyclophosphamide plus methotrexate and 5-fluorouracil); CAF or FAC (cyclophosphamide, Adriamycin® (doxorubicin), and 5-fluorouracil); AC (Adriamycin® and cyclophosphamide); ACT (Adriamycin® plus cyclophosphamide and tamoxifen); AC taxol (Adriamycin® plus cyclophosphamide and paclitaxel (Taxol®)); FACT (5-fluorouracil plus Adriamycin®, cyclophosphamide, and tamoxifen); A-CMF or Adria/CMF (4 cycles of Adriamycin® followed by 8 cycles of CMF); CMFP (CMF plus prednisone); CMFVP (CMF plus vincristine and prednisone); CAFMV (CAF plus methotrexate and vincristine); CMF-VATN (CMF plus vincristine, Adriamycin®, thiotepa, and tamoxifen); MF (methotrexate plus 5-fluorouracil and leucovorin).

Medicines use to relieve side effects caused by chemotherapy include anti-nausea drugs (e.g., reglan), anti-anemia drugs (e.g., epoetin alfa [Procrit®, Epogen®]), and cell-protecting drugs (e.g., amifostin [Ethyol®]).

Examples of additional anticancer drugs that can be used in breast cancer therapy include: alkylating agents including cyclophosphamide (Cytoxan®), ifosphamide (Ifex®), melphalan (L-Pam®), thiotepa (Thioplex®), cisplatin (Cisplatinum®, Platinol®), carboplatin (Paraplatin®), and carmustine (BCNU; BiCNU®); antimetabolites including 5-Fluorouracil (5-FU) methotrexate and edatrexate; antitumor antibiotics including doxorubicin (Adriamycin®) and mitomycin C (Mutamycin®); cytotoxics including mitoxantrone (Novantrone®); vinca alkaloids including vincristine (Oncovin®), vinblastine (Velban®) and vinorelbine (Navelbine®); taxanes including paclitaxel (Taxol®) and docetaxel (Taxotere®); retinoids including fenretinide, corticosteroids including prednisone; antiestrogens including tamoxifen (Nolvadex®); male hormones including fluoxymesterone (Halotestin®); topoisomerase-I compounds including topotecan, irinotecan, 9-amino-camptothecin [9-AC]; anthrapyrazoles including biantrazole and losoxantrone; epidophylotoxins including etoposide and teniposide and angiogenesis inhibitors including compounds that block growth promoting receptors (e.g., PDGF-R and VEGF-R) such as sunitinib (Sutent®).

Hormonal medications also may be used in treatment. If the patient is ER/PR-negative, then chemotherapy usually is given without hormone therapy, however, hormone therapy may be suitable for patients who are in poor health or who have a short projected survival time. In addition to tamoxifen (Nolvadex®), such drugs include: aromatase inhibitors including anastrozole (Arimidex®) and aminoglutethimide (Cytadren®); luteinizing hormone-releasing hormone-inhibiting compounds including goserelin (Zoladex®) and leuprolide (Lupron®); progestins including megestrol acetate (Megace®) and medroxyprogesterone acetate (Provera®); and androgens including fluoxymesterone (Halotestin®), testolactone (Teslac®), and testosterone enanthate (Delatestryl®).

For tumors that are c-erbB2 (HER2) positive, trastuzumab (Herceptin®), a humanized monoclonal antibody against the extracellular domain of HER2, can be used.

EXAMPLES

Example 1

CT-X Antigen Expression in the Massively Parallel Signature Sequencing (MPSS) Data To determine the expression pattern of CT antigens in breast tissue, we initially interrogated our high throughput sequencing data set (Jongeneel et al., Genome Res (2005) 15, 1007-1014; Grigoriadis et al., Breast Cancer Res (2006) 8, R56). These data were derived from a pool of normal human breast luminal epithelial cells, a pool of predominantly ER-positive epithelial enriched primary breast tumors and four breast epithelial cell lines. The majority of CT antigens were not expressed. Sequence tags corresponding to six of the 83 CT-X antigens, included CSAG1 (expressed at 15 transcripts per million (tpm)), CSAG2 (680 tpm), PASD1 (24 tpm), MAGEA2, A3, A6, A 12 (1646 tpm), CT45 (263 tpm) and FMR1NB/NY-SAR-35 (11 tpm), all of which are located on the X chromosome.

Example 2

CT-X Antigen Expression in Breast Cancer Gene Expression Studies

We analyzed the expression of CT-X antigens within a published Affymetrix microarray dataset of 51 breast cancer cell lines, where 41 of the 83 CT-X antigens were represented by 59 probe sets (Neve et al., Cancer Cell (2006) 10, 515-527). We scored a cell line positive for CT-X antigen expression when its $\log_2$ ratio was above the median value, as shown in FIG. 1A and Table 6. The data demonstrate the following broad characteristics for CT-X expression: 1) that about half the lines are completely negative for any of the CT-X genes and the other half express multiple genes; 2) that the MAGEA genes are the most frequently expressed and that about half the lines express MAGEA also express NY-ESO-1/CTAG1B; 3) that all other CT-X antigens on the chip are strongly expressed in not more than 10% of the cell lines tested; 4) that MAGEA and NY-ESO-1/CTAG1B expression is somewhat more frequent in the ER-negative than ER-positive lines with this tendency being more pronounced for NY-ESO-1/CTAG1B. The lines used in the survey contain a higher proportion of ER-negative specimens than occurs in randomly sampled breast cancers and thus might have over represented CT-X antigen positivity. Nevertheless, the data prompted us to undertake a broad survey of MAGEA and NY-ESO-1/CTAG1B gene expression in material derived from fresh breast tumors, based on a similar analysis of Affymetrix data.

Figures 1, 1B:
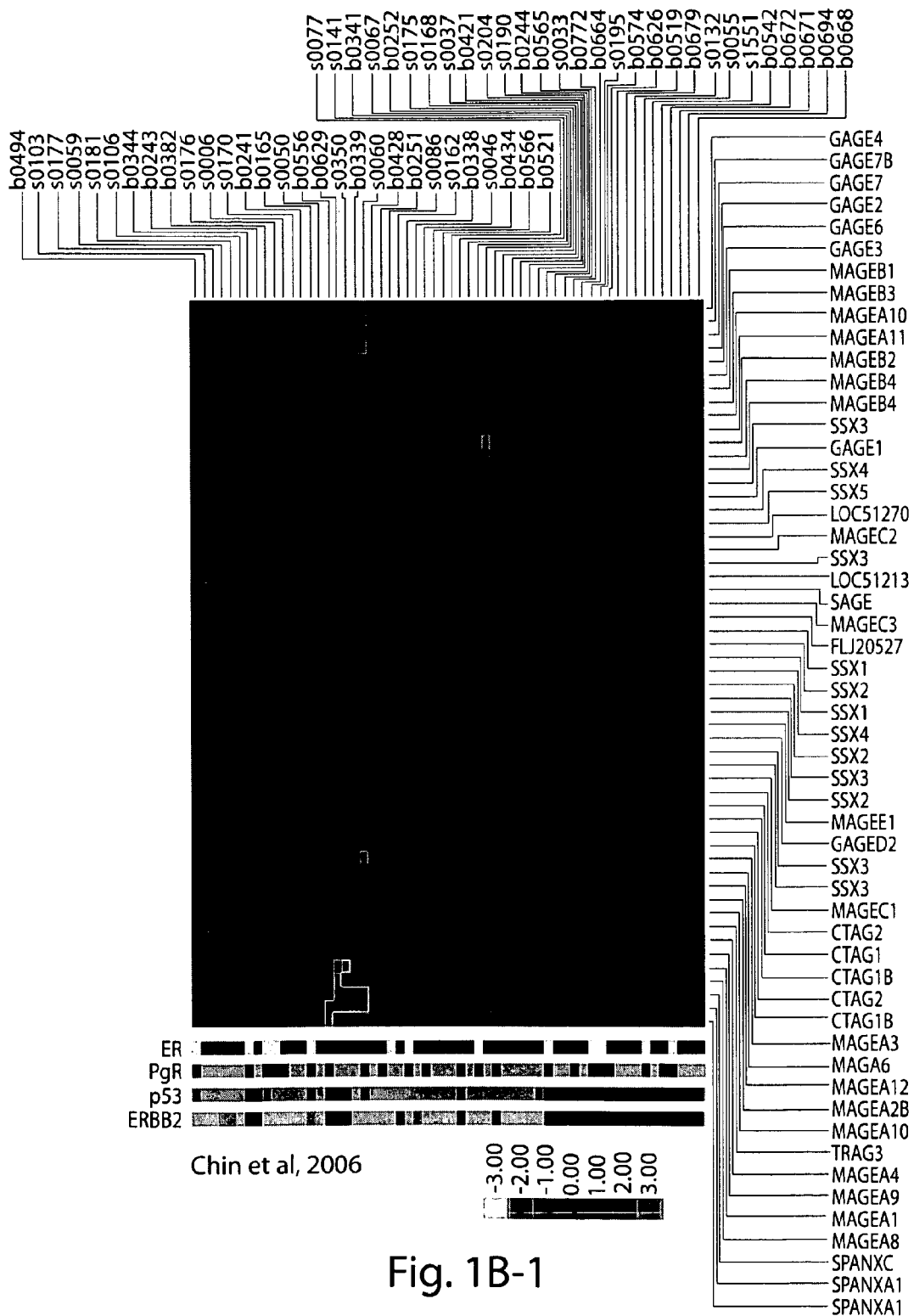
FIG. 1. Expression of CT-X antigens in ER-negative breast cancers cell lines and tumors. High mRNA expression of CT-X antigens are enriched in ER-negative breast cancers across multiple microarray profiling data sets.
Figures 1, 1B, 2:
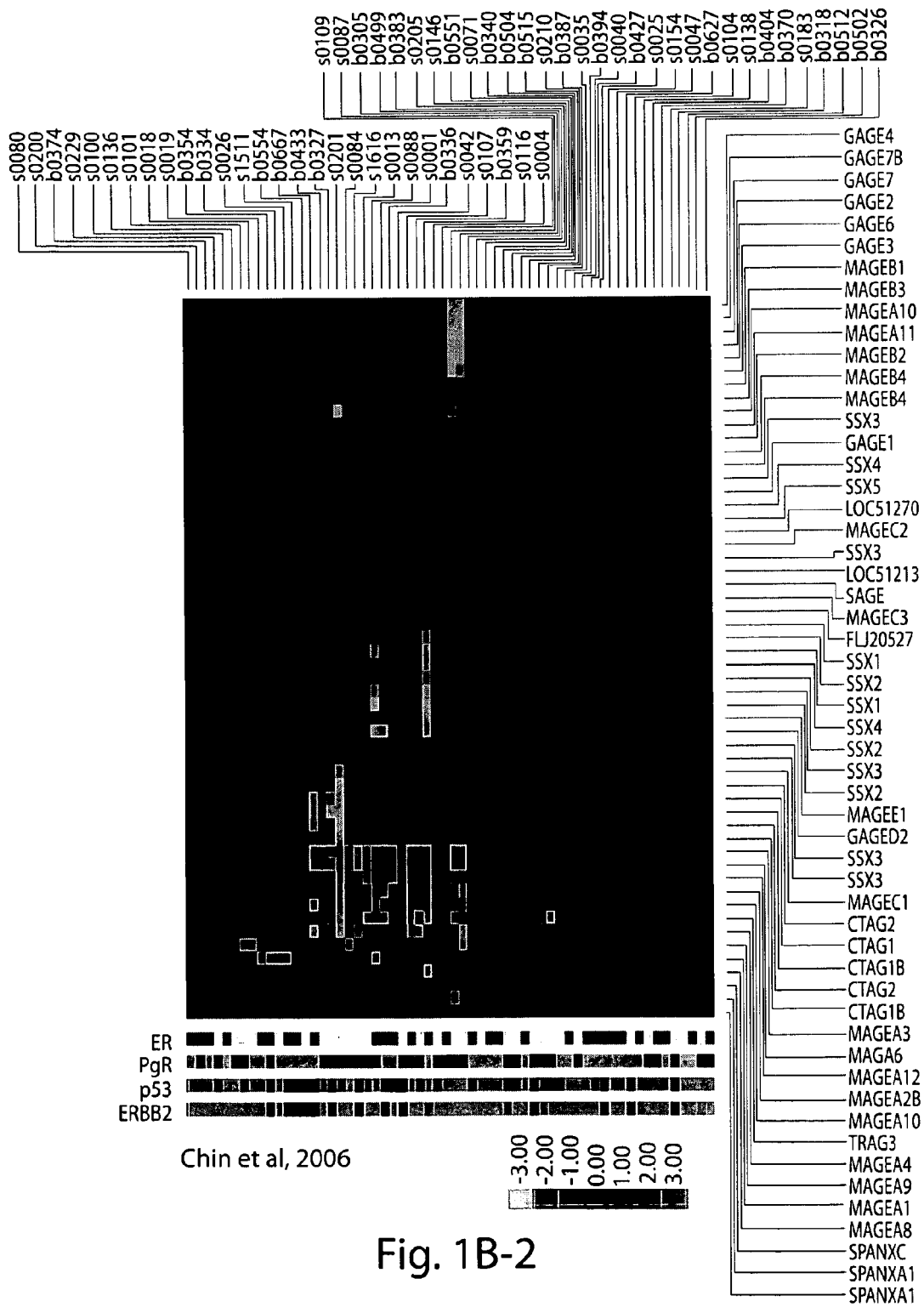
FIG. 2. Heatmap visualization of expression profiles of selected CT-X antigens in patients from the Uppsala cohort. Tumors are in columns, genes are in rows. For each gene, the expression value is mean-centered across the tumors. Dark gray indicates above-mean expression; light gray indicates below-mean expression. The degree of gray-saturation reflects the magnitude of expression level.
Figures 1, 1C:
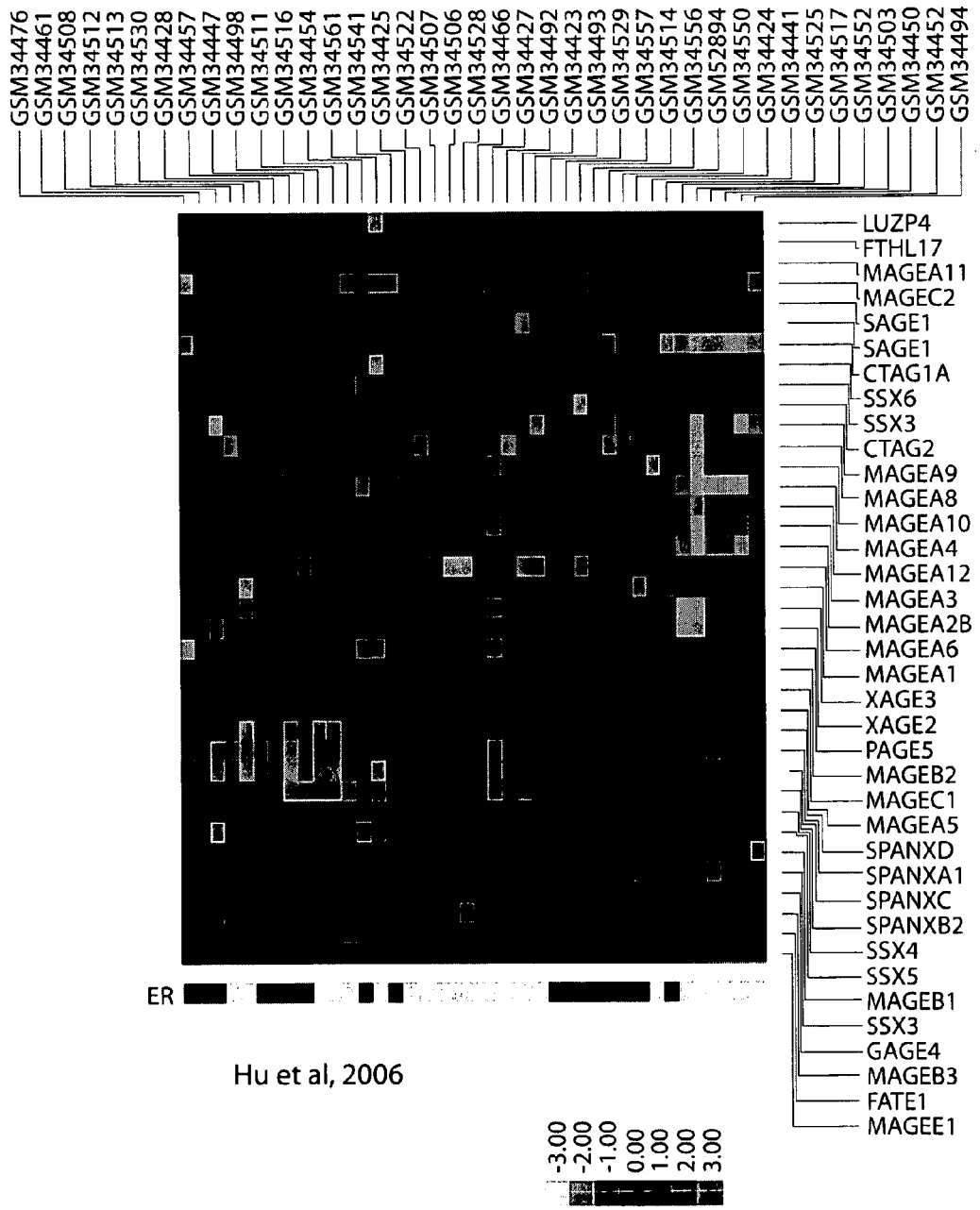
Figures 1, 1C, 2:
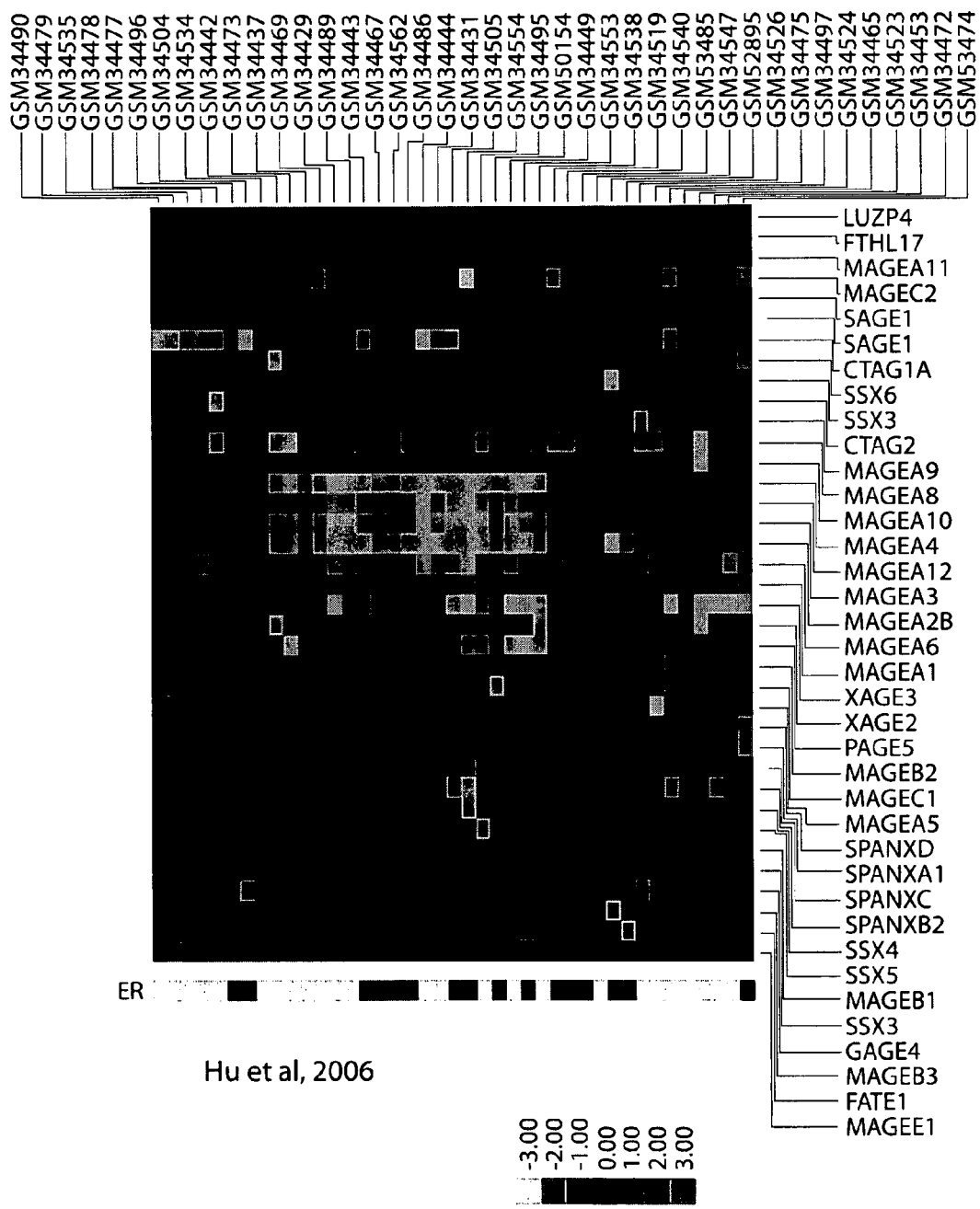
Figures 1, 1D, 2:
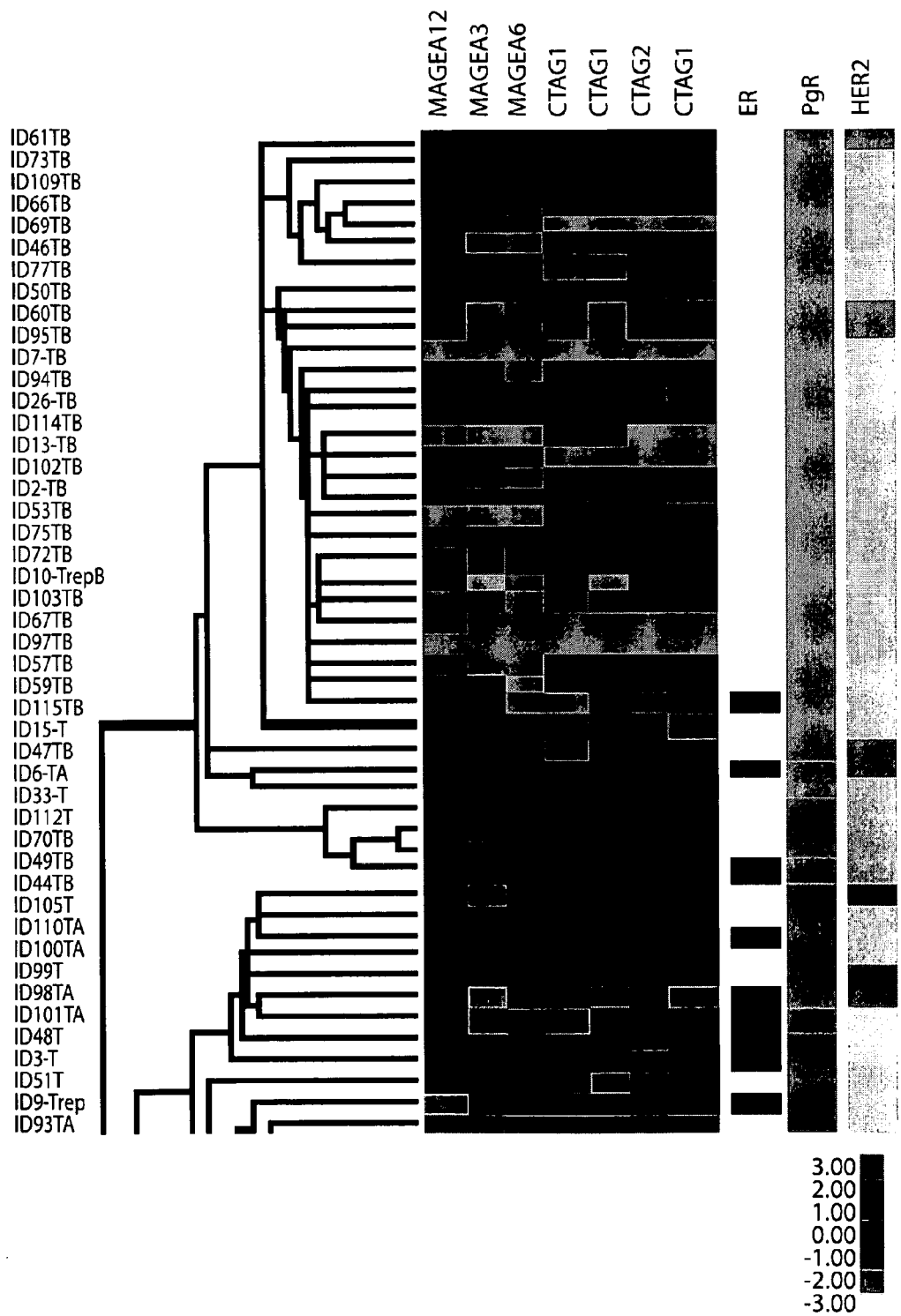
Figures 1, 2:
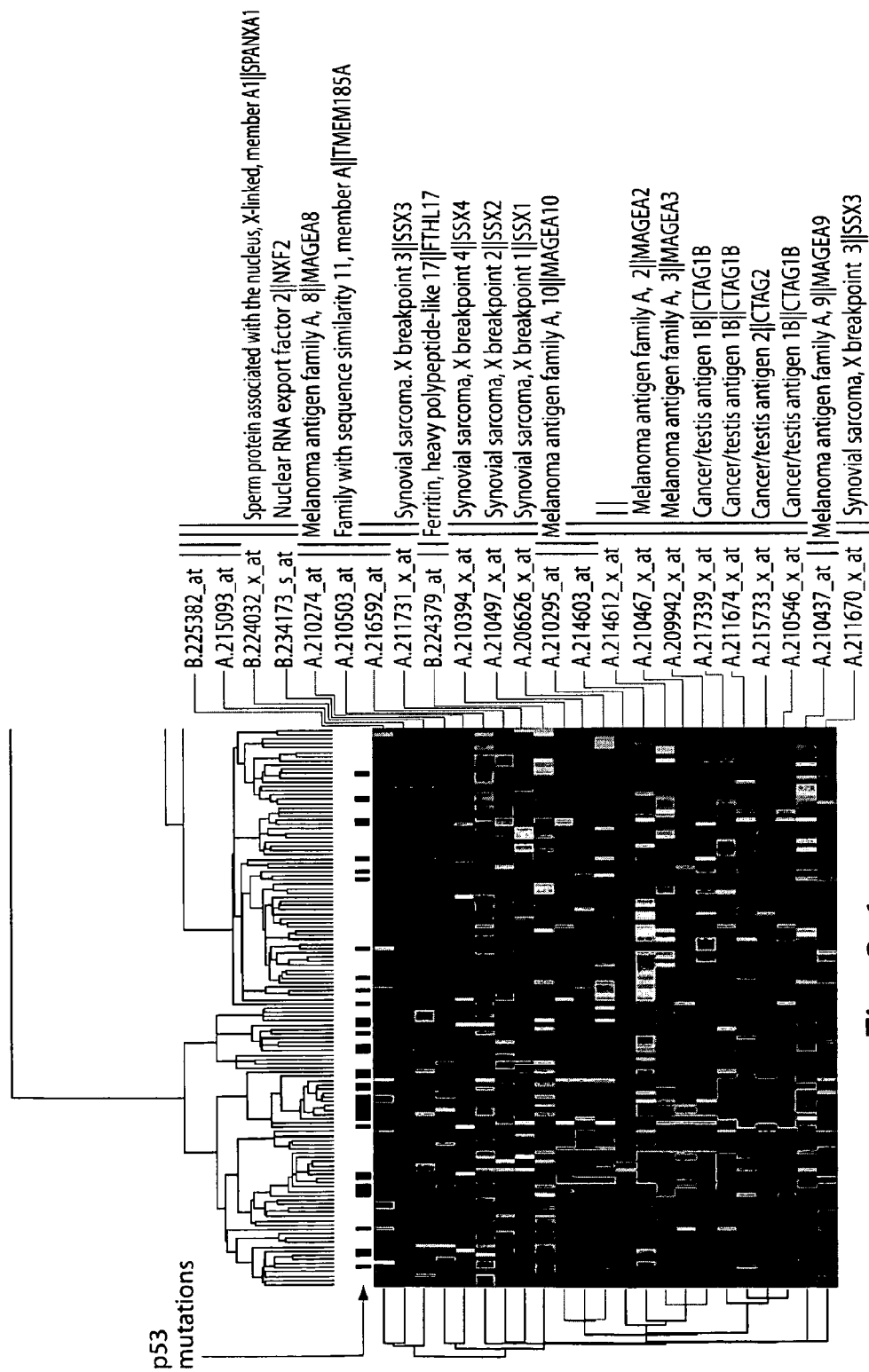
Figure 2:
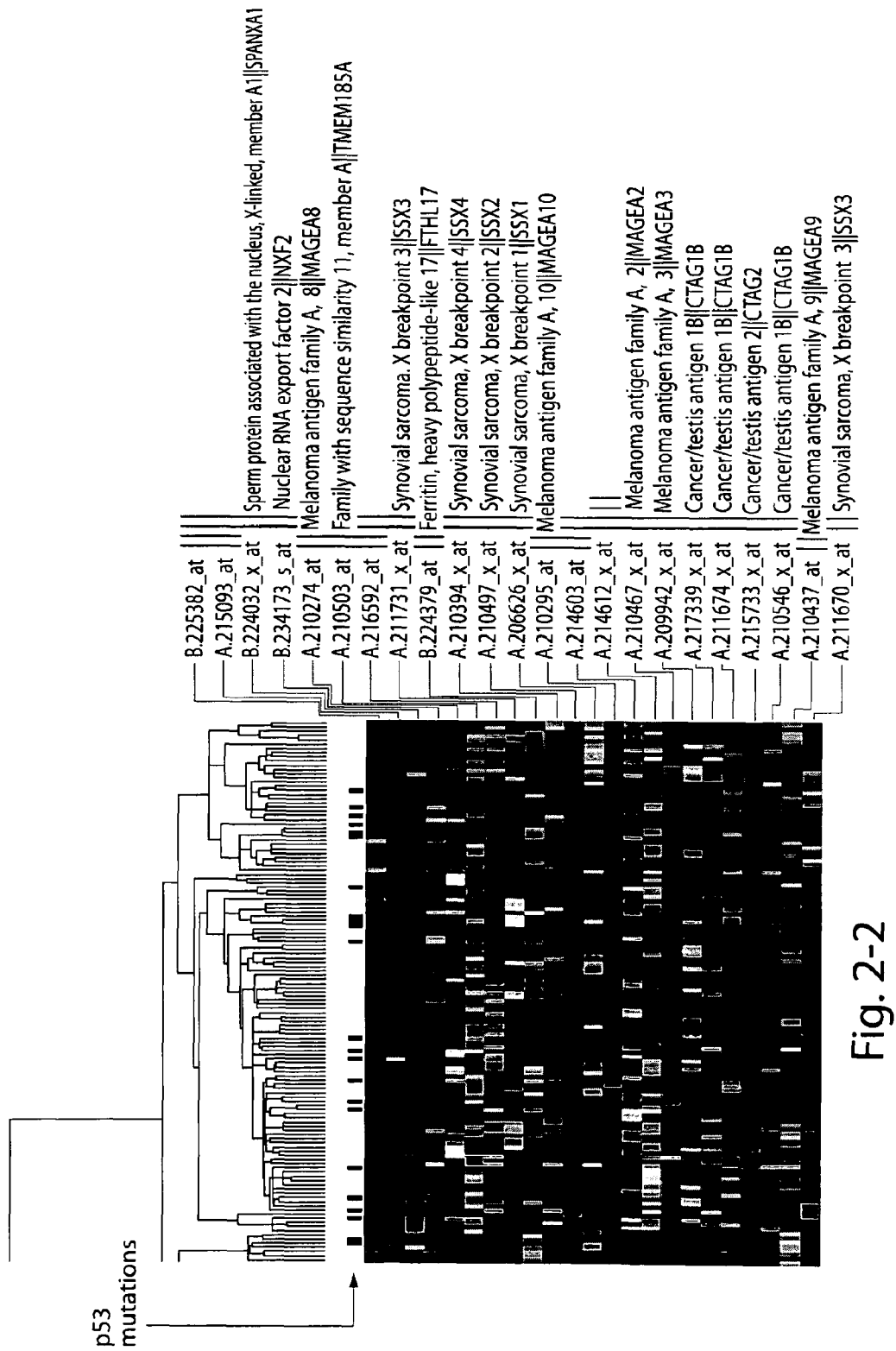

As a first step we interrogated the data published by Doane (Doane et al., Oncogene (2006) 25, 3994-4008) who analyzed a set of 99 breast tumors. As can be seen in FIG. 1D, around 20% of these were positive for MAGEA with a somewhat lower percentage being positive for NY-ESO-1/CTAG1B, the majority of which were also positive for MAGEA. As with the cell lines, the majority of the CT-X positive tumors were ER negative. We then examined eleven published microarray-based gene expression datasets derived from a total of 1,976 primary breast cancers using Oncomine (Rhodes et al., Neoplasia NY, N.Y. (2004) 6, 1-6). As shown in Table 1, overall MAGEA genes were found to be positive in around 13% of tumors with NY-ESO-1/CTAG1B being positive in approximately half that number. There was a strong bias of CT-X antigen expression towards the ER-negative cases with approximately 25% being positive for MAGEA and 14% for NY-ESO-1/CTAG1B with the percentage of ER-negative compared with ER-positive cases positive for antigen expression being three times higher for MAGEA and four times higher for NY-ESO-1/CTAG1B. This distribution was uniform with the proportion of CT-X positive tumors being higher in ER-negative than ER-positive tumors in each of the individual studies included. This bias towards CT-X expression in the ER-negative tumors was also evident by comparison of the averaged level of expression of the antigens in the two tumor types with the combined p-values statistically significant ($p<0.05$) for MAGEA and for NY-ESO-1/CTAG1B.

Due to the listing of additional clinical data in the breast cancer studies surveyed, a number of additional variables were interrogated in relation to CT-X expression (Table 1). It was found that both MAGEA and NY-ESO-1/CTAG1B exhibited more frequent and higher levels of expression in poorly differentiated as compared with well differentiated tumors. In addition there was more frequent expression and higher levels of expression in PR-negative than in PR-positive tumors, in p53 mutated than in p53 normal tumors and in patients who had died than those that were alive. In addition, NY-ESO-1/CTAG1B, but not MAGEA, was more frequently positive in lymph node negative than lymph node positive patients.

Example 3

Meta-analysis of Breast Cancer Microarray Studies

Figures 1, 4:
FIG. 4. CT-X antigen expression over several publicly available breast cancer cohorts (data obtained from Oncomine http://www.oncomine.org). The ER-status is indicated: Light gray indicates ER$^-$ and dark gray indicates ER$^+$ breast tumors, the intermediate gray indicates normal breast samples.
Figures 2, 4:
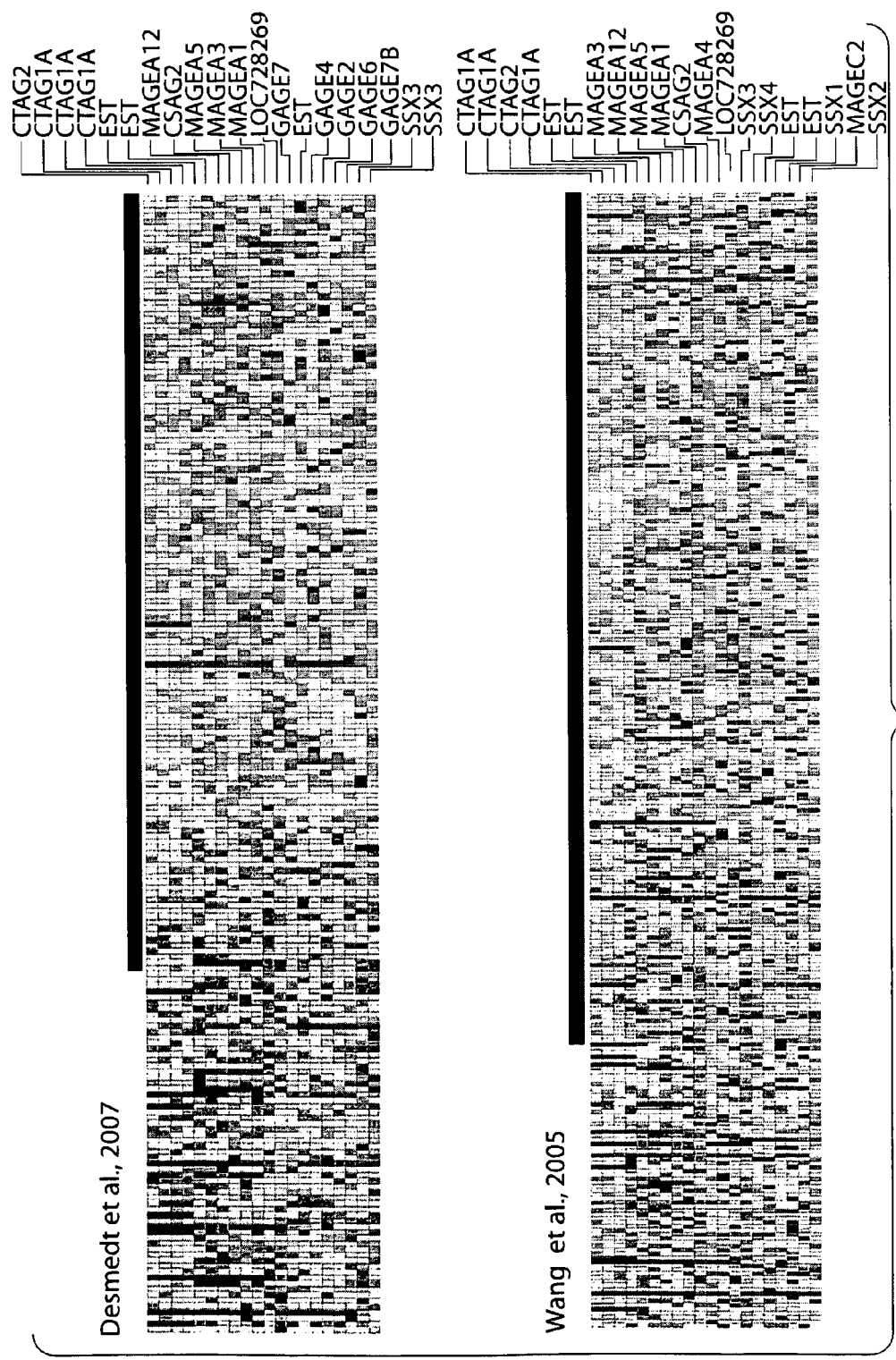
Figures 3, 4:
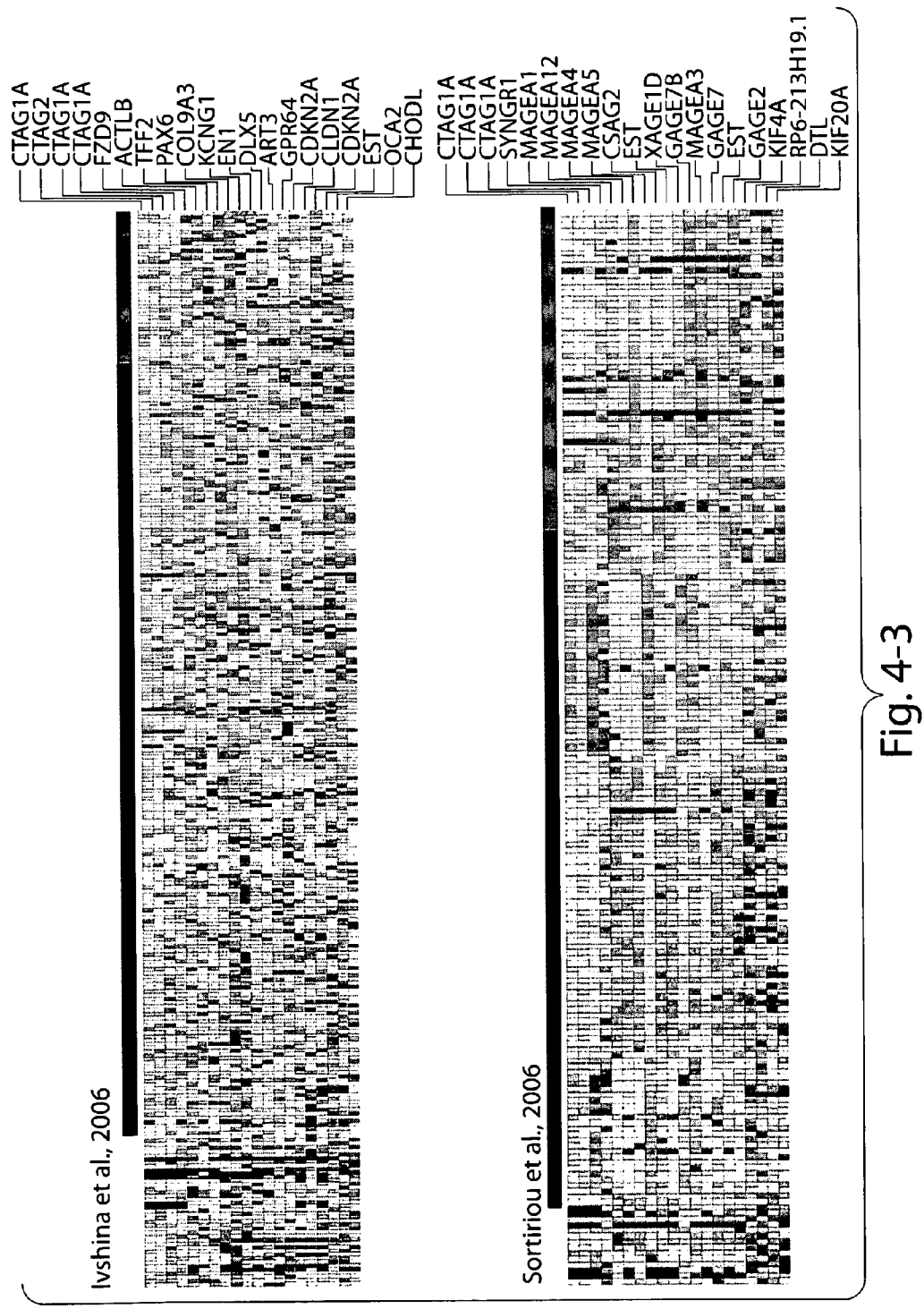

To date, 54 CT-X antigens are known of which 42 were represented by 54 probe sets on the Affymetrix Human Genome U133 set and 38 by 40 probes on the Agilent Human 1A Oligo UNC custom Microarrays (Table 10). We initially analyzed the gene expression levels of these probes in four publicly available data sets (Hu et al., BMC Genomics (2006) 7, 96). In all four, the MAGE-A and NY-ESO-1 families (CTAG1 and CTAG2) were the most frequently expressed CT-X antigens and their expression was mostly found in ER-negative breast tumors (FIG. 1). 18/25 MAGE and CTAG expressing breast cell lines were ER-negative in the Neve et al. data (FIG. 1a), as were 10/21 breast tumors in the Chin et al. set (FIG. 1b) and 10/16 breast tumors in the Hu et al. set (FIG. 1c). The result was even more striking in the Doane et al. study (FIG. 1d) where CTAG1 and CTAG2 expressing breast tumors were ER-negative, although according to their expression profile these tumour samples clustered with in the ER-positive branch. To expand our CT-X expression analysis in breast cancer, data sets within the Oncomine database (www.oncomine.org/main/index.jsp) were interrogated. In six data sets (indicated with a * in Table 11) our initial result was confirmed, namely that CT-X antigen encoding genes are predominantly expressed in ER-negative breast tumours (FIG. 4). CTAG1A and MAGEA3, the most consistently expressed genes over these several breast cohorts, were with the exception of Wang et al. (*Lancet* (2005) 365, 671-679) also significantly differentially expressed between ER-positive and ER-negative breast tumors (Table 11).

Example 4

CT-X Antigen Expression in Molecular Subtypes of Breast Cancers

Using molecular profiling, breast cancers can be subdivided into luminal, HER2-positive, basal-like and so-called normal breast-like tumors (Perou et al., *Nature* (2000) 406, 747-752; Sorlie et al., *PNAS* (2003) 100, 8418-8423).

Figure 5:
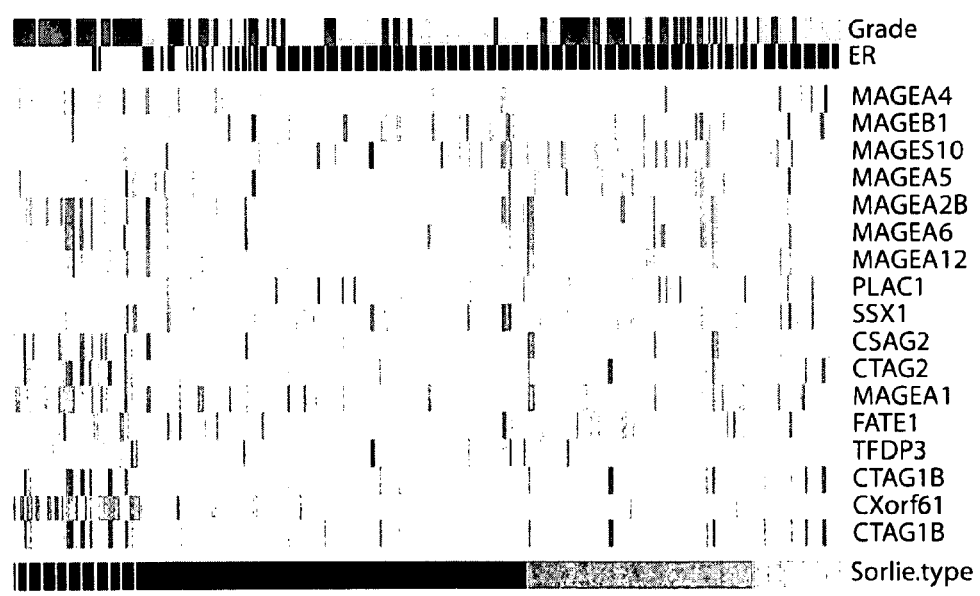
FIG. 5. CT-X antigen expression in breast tumor subtypes. The van de Vijver data set (van de Vijver et al., *NE J Med* (2002) 347, 1999-2009) was used to determine distribution of CT-X antigen expression. The bar at the bottom indicate the five subtypes defined by Sorlie et al. (Sorlie et al., *PNAS* (2003) 100, 8418-8423) in different shades of gray, from left to right: basal-like; HER-positive 2; luminal A; luminal B; and normal-like subtype. In the expression matrix, red indicates increased and blue decreased CT-X antigen expression. The upper bars show biological and clinical aspects of the tumors. For ER status: Dark gray and light gray represent a positive and negative status for ER. For Grade: while gold, light and dark green represent grade 1, 2 and 3.
Figure 6A:
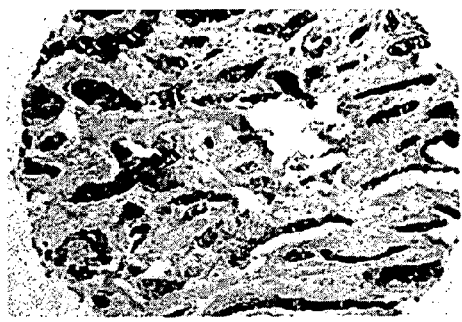
FIG. 6. Expression of MAGEA, NY-ESO-1/CTAG1B and p53 in primary and metastatic breast tumors. IHC staining showing expression of MAGEA, NY-ESO-1/CTAG1B and p53 in primary invasive ductal (A) ×10; (B) ×20; (C) ×100; and metastatic breast carcinomas (D) ×10; (E) ×20; (F) ×100. NY-ESO-1/CTAG1B shows nuclear staining, whereas MAGEA and p53 are seen in the cytoplasm.
Figure 6D:
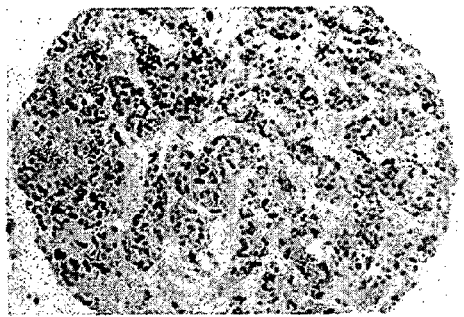
Figure 6B:
Figure 6E:
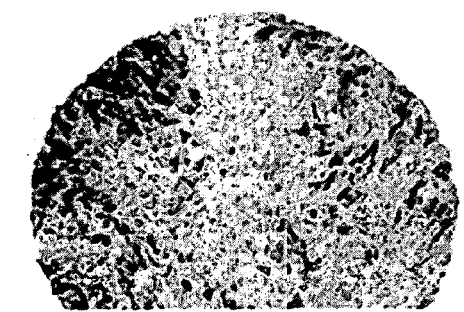
Figure 6C:
Figure 6F:
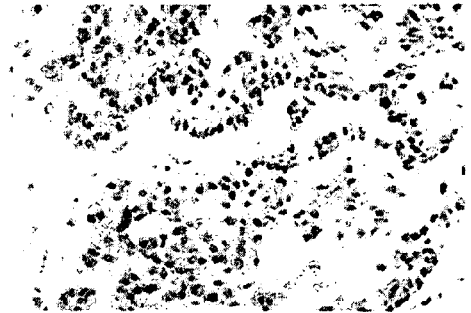

We were able to evaluate whether the expression of CT-X antigens is subtype-specific using the van de Vijver dataset (van de Vijver et al., *NE J Med* (2002) 347, 1999-2009). The correlation of CT antigen expression with the different breast cancer subtypes in the van de Vijver data was tested with Anova analysis. A significant correlation of CT-X expression with the basal subgroup was confirmed for MAGEA4 ($p=0.001$); MAGEA10 ($p=0.022$); MAGEA5 ($p=0.013$); MAGEA2B ($p<0.001$); MAGEA5 ($p=0.013$); MAGEA6 ($p=0.01$); MAGEA12 ($p=0.046$); CTAG2 ($p=0.001$); MAGEA1 ($p=0.011$) and CTAG1B/NY-ESO-1 ($p<0.001$). Such tumors are of a higher grade and predominantly ER-negative (FIG. 5).

Example 5

CT-X Antigen Expression in a Population-based Cohort

Interrogation of data from the Oncomine database showed that the CTAG1, CTAG2 and MAGEA3 expression was also associated with tumor grade and p53 mutations in the Ivshina and Sortiriou data sets (Ivshina et al., *Cancer Res* (2006) 66, 10292-10301; Sotiriou et al., *J Nat Cancer Inst* (2006) 98, 262-272). To investigate this in more detail, we analyzed the expression of CT-X antigens in 258 tumor samples from a further cohort of patients with detailed clinicopathological characteristics (Miller et al., *PNAS* (2005) 102, 13550-13555). High expression of CT-X antigens was confirmed to be associated with ER and PR negativity, poor histological grade and high proliferative activity (Table 1). The CT-X antigens most frequently associated with ER/PR negativity, p53 mutations, tumor grade and proliferative status were again NY-ESO-1, members of MAGEA family and also LAGE1. No significant correlation of CT-X expression with HER2/ERBB2 status was detected. Some of the CT-X antigens tended to have correlated expression patterns as also seen by expression profiling (FIG. 2). Significant ($p<0.05$) and near significant ($p<0.1$) correlations were observed between high expression of members of the MAGEA family (A3, A5 and A9), SSX (1, 2, 3 and 5), NY-ESO-1 (CTAG1B and LAGE1) and FTHL17 and poor outcome as measured by distant metastasis-free survival rates (Table 9).

Example 6

Immunohistochemical Demonstration of CT Antigens in Tissue Arrays of Breast Cancer To confirm CT-X antigen expression in breast cancer at the tissue level, three immunohistochemical (IHC) studies were carried out to complement the gene expression studies. The second and third studies built on the results obtained from the first. The salient features are summarized in Table 2. In the first study, a series of 153 unselected cases of infiltrating breast carcinomas were examined of which 12 were positive for MAGEA, or NY-ESO-1/CTAG1B or both (FIG. 6, Table 2 and Table 3). CT-X antigen expression was taken as positive when at least 1-2% of the tumor cell population was positively stained. Heterogeneity was a feature for both CT-X antigens. While 103 of the 153 tumors in the series were ER-positive, all but one of the CT-X antigen positive tumors (11/12) fell into the ER/PR-negative category (Table 3). It was notable that p53 expression was more prominent in the CT-X group (FIG. 6, Table 3 and Table 4) and that most had a high proliferative index as assessed by Ki-67 staining. The second series comprised a highly selected group of 19 triple negative breast tumors (ER, PR, and HER2-negative). Antigens of the MAGEA or NY-ESO-1/CTAG1B family were expressed in nine (47%) of these triple negative breast tumors (Table 2). Thirteen of the total set were of the basal type of which five were positive for CT-X antigens (Table 4). The final IHC series consisted of 29 matched pairs of primary breast tumors and their brain metastases. These breast tumors had spread preferentially and/or initially to the brain, a feature not infrequently associated with the basal subtype (van de Vijver et al., *NE J Med* (2002) 347, 1999-2009). Fourteen (48%) of these primary tumors showed MAGEA and/or NY-ESO-1/CTAG1B expression (Table 2). Of these 14 CT-X antigen positive tumors, nine were ER-negative, seven of which were also PR-negative (Table 3). Fifty-three metastatic brain deposits showed an increased frequency of CT-X antigen expression, particularly with respect to NY-ESO-1/CTAG1B. MAGEA and NY-ESO-1/CTAG1B expression individually and combined, was observed in 29, 2, and 4 deposits, respectively. Twenty one of these CT-X positive metastases were ER-negative of which 12 were also PR-negative (Table 4).

The overall distribution of ER-positive and ER-negative tumors positive for MAGEA and NY-ESO-1/CTAG1B is shown in Table 5. The data confirmed the relative frequency of expression and distribution by ER status found by transcriptional analysis, with NY-ESO-1/CTAG1B being expressed more particularly in ER-negative tumors.

Example 7

Figure 3:
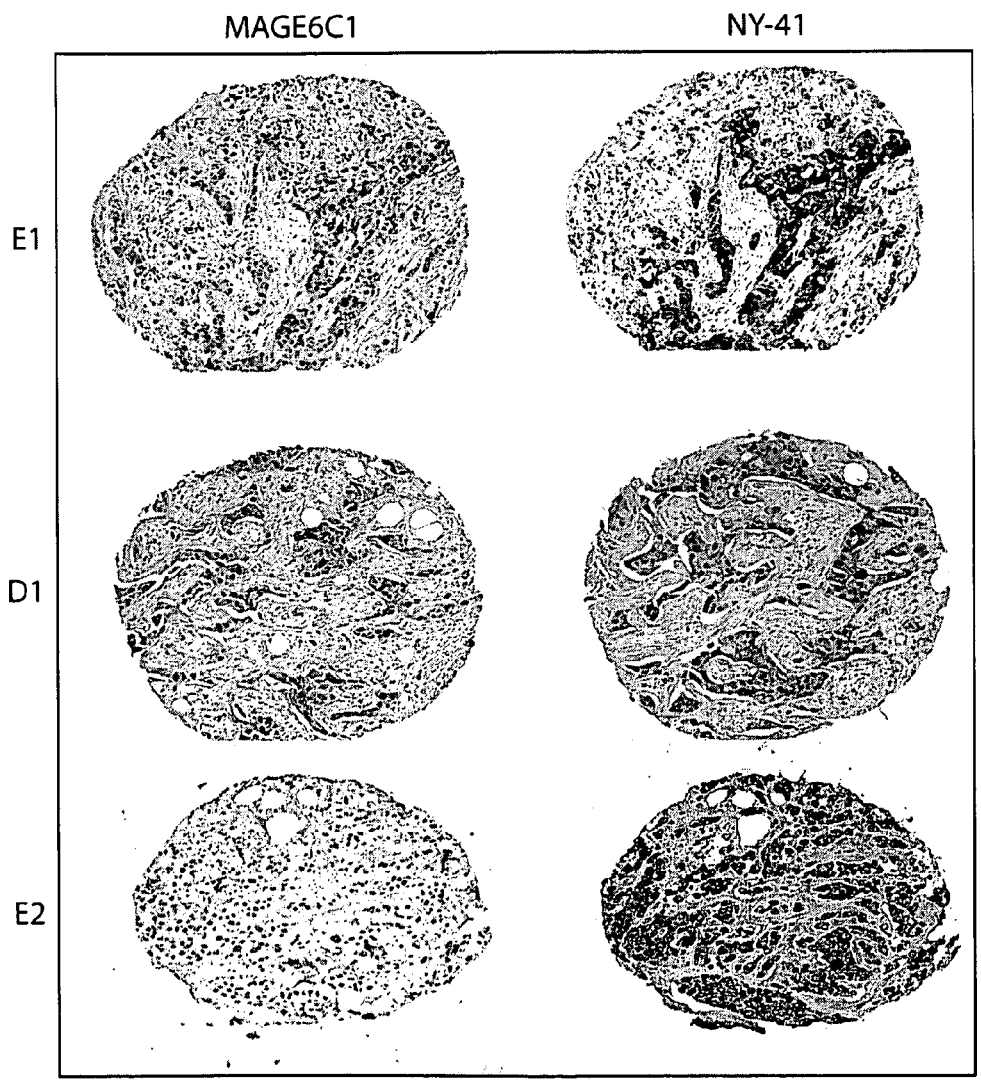
FIG. 3. Immunohistochemical expression of MAGEA (MAGE6C1) and NY-ESO-1 (NY-41) in breast cancer tissues using a tissue microarray. Expression of both proteins is detected in two samples (E1 and D1) and only NY-ESO-1 is detected in sample E2.

Immunohistochemical Analysis of MAGE-A, NY-ESO-1 and CT45 Expression Using Tissue Microarray To further confirm the expression of CT-X antigens in breast cancer tissue, we performed immunohistochemistry of MAGE-A, NY-ESO-1 and CT45 on a tissue microarray containing 168 breast carcinoma samples (FIG. 3). 9/168 (5%) invasive breast carcinomas clearly showed epithelial expression for MAGE-A (7 ER$^-$; 2 ER$^+$), while moderate to strong NY-ESO-1 expression were detected in 6/168 (3.5%; ER$^-$); and weak focal NY-ESO-1 was observed in 9 ER$^+$ cases. CT45 expression was positive in 4 ER$^-$ cases. Excluding the weak NY-ESO-1 positive cases, 12 cases were positive for at least one of the three CT antigens tested. These 12 cases included 10/50 ER$^-$ (20%), and only 2/103 ER$^+$ (2%); $p<0.0001$); and all showed high proliferative index. In contrast, no strong correlation was seen with HER2/ERBB2 status (9/71 HER2$^+$; 3/82 HER2$^-$).

Discussion

The analyses of 51 breast cell lines and the 1,976 breast tumors highlighted the association of steroid receptor negative breast cancer and a propensity to express CT-X antigens. The previous misconception regarding breast cancer and CT antigen poverty almost certainly has arisen as a result of studying consecutive examples of this cancer type when ER-negative tumors will only comprise around 25% of cases. Indeed, the very first immunopathology study of this work exemplifies this conclusion where less than one third of the tumors were ER-negative. As a result, only 8% (12/153) of the lesions were CT-X positive but eleven of the cancers with CT-X expression lacked estrogen receptors (Series 1, Table 3).

On the basis of molecular profiling, Perou and Sorlie and their colleagues have classified breast cancer into five groups, namely luminal A, luminal B, basal-like, HER-2 positive and so-called normal breast-like (Perou et al., *Nature* (2000) 406, 747-752; Sorlie et al., *PNAS* (2003) 100, 8418-8423). Neve and co-workers (Neve et al., *Cancer Cell* (2006) 10, 515-527) have delineated some of the breast cell lines used in the present study (FIG. 1) as being basal-like due to their expression of cytoplasmic components typically found in the basal cells of the normal breast. In our various analyses of the gene arrays, basal-like cell lines and tumors both exhibited higher expression of CT-X antigens. Breast cancers with basal-like features are a recently recognized entity of increasing importance. These lesions are generally of higher grade, have a lower propensity to metastasize to local lymph nodes, exhibit a distinct tendency to spread to brain and carry a very poor prognosis (Fulford et al., *Breast Cancer Res* (2007) 9, R4; Fulford et al., *L G Histopathology* (2006) 49, 22-34; Crabb et al., *Clin Breast Cancer* (2008) 8, 249-256). Usually they are ER- and PR-negative and do not over-express HER-2. Hence, these tumors constitute a subset of the so-called triple negative breast cancers.

The breast tumors that comprise the lesions of Series 2 and 3 are either all examples of triple negative cancers (Series 2) or contain a not infrequent number of such lesions (Series 3). For these cancers therapeutic options are limited. Many are also examples of basal-like cancers. As exemplified by MAGEA and NY-ESO-1/CTAG1B expression, CT-X antigens are frequently present in such tumors (Table 2).

Materials and Methods

Tumour Characteristics.

For microarray analysis, (Uppsala cohort) study population consists of a population-based cohort of primary breast cancer patients receiving primary therapy from 1987 to 1989 in the county of Uppsala, Sweden (Miller et al., *PNAS* (2005) 102, 13550-13555). From the initial set of 315 patients, representing 65% of all breast cancer patients in the Uppsala County during these years, tissues from 258 patients were submitted to array analysis. Clinicopathological variables were obtained from patient records.

Meta-Analysis of CT Expression Using the ONCOMINE Database.

The expression of CT-X antigens in breast cancer tissues was obtained from meta-analysis of a microarray public database (Rhodes et al., *Neoplasia* NY, N.Y. (2004) 6, 1-6). For each of the 50 breast cancer gene expression microarray studies present in the database, we reviewed the samples profiled. Eleven studies that contained both classes of interest (ER-negative and positive samples) and at least 90 samples were further analyzed. Analyses of differential expression of CT-X antigens were conducted following the assignment of samples to ER-negative and -positive classes using Welch t-statistics. Tests were conducted as one-sided for specific over expression analysis (Rhodes et al., *Neoplasia* NY, N.Y. (2004) 6, 1-6). The p-values reflect the significance of the differential expression observed between different classes. Samples were considered CT-X antigen positive when the normalized expression values were greater than 0. Analyses of interest included in addition to ER status, high-grade versus low-grade cancer, lymph node status, PR status, tumor differentiation and outcome. The p-values were also combined to determine the average effect size of the variable across studies (Rosenthal et al., *Psychosom Med* (1991) 53, 247-271).

Immunohistochemistry and Tissue Microarray Analysis.

Routinely fixed paraffin-embedded tissue blocks containing mammary carcinomas excised at the time of surgery were extracted from the files of the Department of Surgical Pathology, Weill-Cornell Medical College (IHC Series 1), from the files of the Department of Pathology, Austin Hospital, Melbourne (IHC Series 2) or from the files of the Department of Pathology, University of Brisbane, Medical Faculty of Charles University in Plzen-Czech Republic, Instituto Nacional do Cancer-Brazil and Laboratorio Salomao Zoppi-Brazil (IHC Series 3). Series 1 and 3 served as donor blocks for the TMAs. The TMAs and Series 2 samples were dewaxed in xylene and rehydrated through alcohols. Antigen retrieval was performed by microwave boiling in 100 mM citrate buffer pH 6.0 for 15 minutes or for Series 2 and 3 in EDTA (pH 8.0) buffer for two minutes. Endogenous peroxidase activity was quenched with 0.3% hydrogen peroxide for 5 minutes. Sections were then incubated with affinity purified NY-ESO-1 specific rabbit polyclonal antibody (NY45) (Series 1) or monoclonal antibodies ES121 or E978 specific to NY-ESO-1 (Series 2 and 3) and monoclonal antibody specific to MAGEA (detecting multiple MAGE-A antigens, including MAGE-A1, A3, A4, A6) (6C1, Santa Cruz Biotechnologies) diluted in Tris-buffered saline with 10% BSA at 1:1000 for one hour at room temperature. The slides were then processed using Dako Envision+™ HRP (DakoCytomation, Glostrup, Denmark), following the manufacturer's protocol, counterstained briefly with Mayer's haematoxylin (Amber Scientific, Belmont, Wash.) and cover slipped. Specimens of known antigen positive tumors were used as a positive control and negative controls were prepared by omission of the primary antibody or by using a relevant subclass negative control. The various antibodies and their source used to demonstrate breast cancer features are shown in Table 7.

Datasets and Gene Annotation.

The CT antigen database (available at: www.cta.lncc.br) (Almeida et al., *Nucl Acids Res* (2008)) was used as a reference to extract data corresponding to the CT-X-encoding genes from the microarray datasets analyzed in this study using mRNA accession numbers as cross-references (Neve et al., *Cancer Cell* (2006) 10, 515-527; Doane et al., *Oncogene* (2006) 25, 3994-4008; van de Vijver et al., *NE J Med* (2002) 347, 1999-2009; Hu et al., *BMC Genomics* (2006) 7, 96; Chin et al., *Cancer Cell* (2006) 10, 529-541; Miller et al., *PNAS* (2005) 102, 13550-13555; Minn et al., *Nature* (2005) 436, 518-524; Wang et al., *Lancet* (2005) 365, 671-679; Desmedt et al., *Clin Cancer Res* (2007) 13, 3207-3214). Similarly, CT-X encoding probes sets were retrieved for the Agilent Human oligonucleotide used in Hu et al., study (Hu et al., *BMC Genomics* (2006) 7, 96) (Table 10). When several probe sets were available for the same gene, all were used for analysis. Extracted data were normalized with the MASS algorithm (Affymetrix. Affymetrix Statistical Algorithms Description Document available at: www.affymetrix.com/support/technical/whitepapers/sadd_whitepaper.pdf) and $\log_2$ transformed.

For visualization purposes, CT-X expression matrices were centered by subtracting the median value for each probe set from each measured value. Hierarchical clustering was used to illustrate commonalities in CT-X gene expression across the data sets, using a modified version of the heatmap.plus package in BioConductor 2.1 (available at: www.bioconductor.org); further data processing and analysis were carried out in R 2.7.0 (available at: www.r-project.org).

Statistical Data Analysis.

Anova and t-tests were used to determine the association between the expression level and clinical and pathological features of breast cancer patients using the STATA software, Version 9 (StataCorp, College Station, Tex., USA). The p-values were adjusted for multiple comparisons using the method of Benjamini and Hochberg, whereby p-values <=0.05 were considered significant. We used a Cox proportional Hazards Model to stratify distant metastasis-free and overall survival for CT-X antigen expressing tumors.

TABLE 1

CT-X expression levels in ER-negative and -positive breast tumors in several microarray studies*

| | CT positive samples** Estrogen Receptor | | Median expression values* | | | |
|---|---|---|---|---|---|---|
| CT-X | Negative | Positive | ERneg | ERpos | P value[&] | Study[$] |
| MAGEA | 24/64 | 10/134 | −0.752 | −1.487 | 0.000002 | Desmedt_Breast |
| | 24/78 | 17/154 | −0.357 | −0.659 | 0.00096 | Bittner_Breast |
| | 9/52 | 0/41 | −0.763 | −0.782 | 0.003 | Boersma_Breast |
| | 10/42 | 3/57 | −1.040 | −1.241 | 0.009 | Minn_Breast_2 |
| | 18/51 | 8/82 | −0.368 | −0.498 | 0.013 | Hess_Breast |
| | 5/34 | 3/85 | −0.736 | −0.785 | 0.053 | Sotiriou_Breast_3 |
| | 7/34 | 12/211 | −0.660 | −0.477 | 0.085 | Ivshina_Breast |
| | 18/69 | 30/226 | −0.413 | −0.602 | 0.165 | vandeVijver_Breast |
| | 10/43 | 7/75 | −0.680 | −0.746 | 0.215 | Chin_Breast |
| | 13/77 | 18/209 | −0.647 | −0.603 | 0.393 | Wang_Breast |
| | 138/544 (25.4%) | 105/1274 (8.2%) | | | 1.1E−10[@] | |
| NY-ESO-1/CTAG1B | 10/69 | 15/226 | −2.030 | −2.720 | 0.00013 | vandeVijver_Breast |
| | 14/42 | 6/57 | −1.539 | −1.700 | 0.00082 | Minn_Breast_2 |
| | 11/64 | 2/134 | −1.553 | −1.604 | 0.002 | Desmedt_Breast |
| | 11/77 | 5/209 | −1.720 | −1.779 | 0.004 | Wang_Breast |
| | 6/34 | 2/211 | −1.584 | −1.671 | 0.011 | Ivshina_Breast |
| | 12/78 | 3/154 | −1.200 | −1.226 | 0.018 | Bittner_Breast |
| | 2/34 | 0/85 | −1.107 | −1.155 | 0.031 | Sotiriou_Breast_3 |
| | 10/48 | 7/110 | −0.587 | −0.715 | 0.0236 | Bild_Breast |
| | 2/52 | 0/41 | −1.031 | −1.046 | 0.047 | Boersma_Breast |
| | 2/43 | 1/75 | −0.693 | −0.696 | 0.234 | Chin_Breast |
| | 5/51 | 2/82 | −0.815 | −0.773 | 0.331 | Hess_Breast |
| | 85/592 (14.4%) | 43/1384 (3.1%) | | | 1E−12[@] | |

| | Grade | | | Median expression values* | | | | |
|---|---|---|---|---|---|---|---|---|
| | 1 | 2 | 3 | Grade 1 | Grade 2 | Grade 3 | P value[&] | Study[$] |
| MAGEA | 2/30 | 9/107 | 39/141 | −0.780 | −0.719 | 0.235 | 0.000023 | Bittner_Breast |
| | 2/67 | 2/46 | 12/59 | −0.864 | −0.820 | −0.770 | 0.000065 | Sotiriou_Breast_3 |
| | 0/2 | 5/54 | 21/77 | −0.497 | −0.495 | −0.373 | 0.02 | Hess_Breast |
| | 3/68 | 6/126 | 10/55 | −0.554 | −0.437 | −0.446 | 0.023 | Ivshina_Breast |
| | 7/167 (4.2%) | 22/330 (6.7%) | 82/332 (24.7%) | | | | 1.15E−09[@] | |
| NY-ESO-1/CTAG1B | 0/68 | 2/126 | 7/55 | −1.995 | −1.950 | −1.910 | 0.00014 | Ivshina_Breast |
| | 1/67 | 1/43 | 6/59 | −1.110 | −1.170 | −1.073 | 0.032 | Sotiriou_Breast_3 |
| | 0/2 | 25/54 | 52/77 | −0.447 | −0.041 | −0.066 | 0.038 | Hess_Breast |
| | 2/30 | 9/107 | 22/141 | −0.876 | −0.986 | −0.963 | 0.11 | Bittner_Breast |
| | 3/167 (1.8%) | 37/330 (11.2) | 87/332 (26.2%) | | | | 0.000011[@] | |

| | Progesterone Receptor | | Median expression values* | | | |
|---|---|---|---|---|---|---|
| | Negative | Positive | PRneg | PRpos | P value[&] | Study[$] |
| MAGEA | 28/108 | 13/122 | −0.476 | −0.620 | 0.02 | Bittner_Breast |
| | 9/42 | 3/57 | −1.091 | −1.241 | 0.088 | Minn_Breast_2 |
| | 12/43 | 4/75 | −0.700 | −0.746 | 0.095 | Chin_Breast |
| | 49/193 (25.4%) | 20/254 (7.9%) | | | 0.003[@] | |
| NY-ESO-1/CTAG1B | 8/108 | 3/122 | −1.152 | −1.293 | 0.001 | Bittner_Breast |
| | 7/42 | 0/57 | −1.911 | −2.026 | 0.002 | Minn_Breast_2 |
| | 2/43 | 1/75 | −0.685 | −0.698 | 0.34 | Chin_Breast |
| | 17/193 (8.81%) | 4/254 (1.6%) | | | 0.000116[@] | |

| | Lymph node status | | Median expression values* | | | |
|---|---|---|---|---|---|---|
| | Negative | Positive | LN negative | LN positive | P value[&] | Study[$] |
| MAGEA | 9/51 | 8/67 | −0.740 | −0.707 | 0.163 | Chin_Breast |
| | 24/151 | 24/144 | −0.593 | −0.503 | 0.327 | vandeVijver_Breast |
| | 11/159 | 7/81 | −0.489 | −0.477 | 0.772 | Ivshina_Breast |

TABLE 1-continued

CT-X expression levels in ER-negative and -positive breast tumors in several microarray studies*

| | | | | | | |
|---|---|---|---|---|---|---|
| NY-ESO-1/CTAG1B | 44/361 (12.2%) | 39/292 (13.4%) | | | 0.346@ | |
| | 9/159 | 0/81 | −1.713 | −1.838 | 0.029 | Ivshina_Breast |
| | 19/151 | 6/144 | −2.596 | −3.125 | 0.062 | vandeVijver_Breast |
| | 3/51 | 0/67 | −0.800 | −0.809 | 0.083 | Chin_Breast |
| | 31/361 (8.6%) | 6/292 (2.0%) | | | 0.003@ | |

| | P53 status | | Median expression values* | | | |
|---|---|---|---|---|---|---|
| | Mutant | WT | Mutant P53 | WT p53 | P value& | Study$ |
| MAGEA | 9/58 (15.5%) | 10/189 (5.3%) | −0.349 | −0.506 | 0.023 | Ivshina_Breast |
| NY-ESO-1/CTAG1B | 6/58 (10.3%) | 2/189 (1.1%) | −1.612 | −1.667 | 0.013 | Ivshina_Breast |

| | Tumor Differentiation | | Median expression values* | | | |
|---|---|---|---|---|---|---|
| | Well and Moderate | Poor | Well/Moderate | Poor | P value& | Study$ |
| MAGEA | 7/113 6.2% | 26/83 31.3% | −1.721/−1.470 | −1.148 | 0.0000065 | Desmedt_Breast |
| NY-ESO-1/CTAG1B | 3/113 2.6% | 9/83 10.8% | −1.557/−1.606 | −0.959 | 0.006 | Desmedt_Breast |

| | Disease-free survival (5 yrs) | | Median expression values* | | | |
|---|---|---|---|---|---|---|
| | Dead | Alive | Dead | Alive | P value& | Study$ |
| MAGEA | 7/69 10.1% | 12/158 7.6% | −0.500 | −0.374 | 0.191 | Ivshina_Breast |
| NY-ESO-1/CTAG1B | 6/69 8.7% | 2/158 1.3% | −1.899 | −1.967 | 0.019 | Ivshina_Breast |

*Normalized expression units
&The p-Value reflects the significance of the differential expression observed between different classes.
**Samples were considered CT-X positive when the normalized expression values were greater than 0.
@The pvalues were combined to determine the average effect size of the variable across studies
$Datasets obtained from Oncomine (http://www.oncomine.org) (Sotiriou et al., J Nat Cancer Inst (2006) 8, R56)
Bild_Breast (Bild et al., Nature (2006) 439, 353-357)
Bittner_Breast (https://expo.intgen.org/expo/public/)
Boersma_Breast (Boersma et al., Intern J Cancer (2008) 122, 1324-1332)
Chin_Breast (Chin et al., Cancer Cell (2006) 10, 529-541)
Desmedt_Breast (Desmedt et al., Clin Cancer Res (2007) 13, 3207-3214)
Hess_Breast (Hess et al., J Clin Oncol (2006) 24, 4236-424447)
Ivshina_Breast (Ivshina et al., Cancer Res (2006) 66, 10292-10301)
Minn_Breast_2 (Minn et al., Nature (2005) 436, 518-524)
Sotiriou_Breast_3 (Sotiriou et al., J Nat Cancer Inst (2006) 98, 262-272)
van deVijver_Breast (van de Vijver et al., NE J Med (2002) 347, 1999-2009)
Wang_Breast (Wang et al., Lancet (2005) 365, 671-679)

TABLE 2

Immunohistochemistry expression of CT antigens in breast cancer

| | | | No. of tumors with expression | | | Number (%) |
|---|---|---|---|---|---|---|
| Series | Tumor Description | n= | MAGE-A | NY-ESO-1 | MAGE-A/ NY-ESO-1 | MAGE-A/ NY-ESO-1 |
| 1 | Primary | 153 | 6 | 3 | 3 | 12 (8) |
| 2 | Primary | 19 | 3 | 4 | 2 | 9 (47) |
| 3a | Primary | 29 | 13 | 0 | 1 | 14 (45) |
| 3b | Brain mets from 3a | 53 | 29 | 2 | 4 | 35 (66) |

TABLE 3

Characteristics of tumors positive for MAGE-A or NY-ESO-1 antigens by immunohistochemistry

| Series | Tumor Description | MAGE-A or NY-ESO-1 positive | Tumor characteristics | | | |
|---|---|---|---|---|---|---|
| | | | ER neg | P53 pos | Basal | ER neg Basal |
| 1 | Primary | 12 | 11 | 10 | ND[(1)] | ND[(1)] |
| 2 | Primary | 9 | 9* | ND[(1)] | 5 | 5 |
| 3a | Primary | 14 | 9** | 9 | 10 | 7 |
| 3b | Brain mets from 3a | 35 | 21*** | 16 | 25 | 12 |

*Also PR negative
**7/9 also PR negative
***12/21 also PR negative
[(1)]Not done

TABLE 4

Characteristics of tumors included in the immunohistochemistry series.

| Series | Tumor Description | n= | Tumor characteristics | | | | |
|---|---|---|---|---|---|---|---|
| | | | ER neg | P53 pos | HER2 neg | Basal | EGFR pos |
| 1 | Primary | 153 | 50 | 66 | ND | ND | ND |
| 2 | Primary | 19 | 19 | ND | 19 | 13 | 16 |
| 3a | Primary (Initial mets to brain) | 29 | 16 | 17 | 12 | 19 | 1 |
| 3b | Brain mets from 3a | 53 | 30 | 23 | 42 | 34 | 4 |

TABLE 5

Overall distribution of MAGEA and NY-ESO-1/CTAG1B positive tumors by ER status.

| Tumor Description | | CT-X positivity | |
|---|---|---|---|
| | | MAGEA | NY-ESO-1/CTAG1B |
| Primaries | ER-negative | 23 | 3 |
| | ER-positive | 5 | 0 |
| Metastases | ER-negative | 19 | 2 |
| | ER-positive | 11 | 0 |

TABLE 6

CT-X antigen expression in breast cancer cell lines*

| CT-X antigen family | Genes | Cell Lines | |
|---|---|---|---|
| | | ER-negative | ER-positive |
| MAGEA | MAGEA 2B, 3, 6, 8, 9, 10, 11 | HCC1500, HCC38, HCC202, HCC3153, HCC1954, HCC70, SUM225CWN, SUM159PT, SUM1315MO2, SUM185PE, MDAMB231, MDAMB157, MDAMB436, MDAMB435, MDAMB468, HS578T, BT20, AU565, SKBR3 | HCC1428, HCC1007, BT483, ZR751, ZR75B, LY2 |
| NY-ESO-1 | CTAG1B, CTAG1A, CTAG2 | HS578T, MDAMB157, MDAMB435, HCC1187, AU565, SUM225CWN, SUM1315MO2, SKBR3 | HCC1428 |
| CSAG | CSAGE2 | HS578T, AU565, HCC1428, MDAMB435, SUM225, SKBR3, SUM1315MO2 | |
| CXorf48 | CXorf48 | HS578T | |
| GAGE | GAGE-2, -3, -5, -6, -7 | HS578T, AU565, SUM159PT, MDAMB157, HCC202, HCC1187, SUM185PE, MDAMB435 | T47D, HCC1428 |
| MAGEB | MAGEB 1, 2, 3, 4 | MDAMB231, AU565 | |
| MAGEC | MAGEC1 | SUM159PT, MDAMB231, MDAMB435 | |
| MAGEC | MAGEC2 | HCC1500, SUM225CWN, SUM159PT, MDAMB157, AU565 | |
| MAGEC | MAGEC2 | HCC1500, SUM225CWN, SUM159PT, MDAMB157, AU565 | |
| SPANX | SPANXA1, SPANXC | SUM159PT, MDAMB157, MDAMB231, HCC1500 | MDAMB415 |
| SSX | SSX1, -2, -3, -4, -5 | HCC1007, HS578T, AU656, MDAMB415 | |
| XAGE | XAGE1 | HCC1500, AU565, SUM159PT, MDAMB231, | HCC1007, HCC1428, T47D |

*Cell lines positive for CT antigens. Cell lines highlighted in bold and italic were classified as basal as defined by Neve et al (Cancer Cell (2006) 10, 515-527.

TABLE 7

Antibody reagents used to demonstrate breast cancer functional indices

| Antibody | Company | Clone - Dilution |
|---|---|---|
| PR | Novocastra | 1A6 - 1:500 |
| ER | Novocastra | 6F11 - 1:100 |
| HER2 | DAKO | Herceptest ™ |
| p63 | DAKO | 4AL - 1:400 |
| SMA | DAKO | 1A4 - 1:100 |
| CK5/6 | DAKO | D5/16B4 - 1:50 |
| CK14 | Neomarkers | LL002 - 1:50 |
| EGFR | Zymed | 31G7 - 1:50 |

TABLE 8

Statistical analysis of clinicopathological data with CT-X antigen expression

| | positive | negative | p-value |
|---|---|---|---|
| | Estrogen receptor | | |
| | n = 217 | n = 37 | |
| MAGEA9 A_210437_at | 4.44 (0.84) | 4.90 (0.88) | 0.0276 |
| CTAG1B A_210546_x_at | 3.10 (0.69) | 4.07 (2.12) | <0.0001 |
| CTAG1B A_211674_x_at | 3.46 (0.77) | 4.25 (2.19) | 0.0030 |
| CTAG2 A_215733_x_at | 3.37 (0.59) | 4.09 (1.63) | 0.0001 |
| CTAG1B A_217339_x_at | 3.55 (0.64) | 4.32 (1.69) | 0.0001 |
| | Progesterone receptor | | |
| | n = 197 | n = 67 | |
| MAGEA9 A_210437_at | 4.41 (0.82) | 4.78 (0.90) | 0.0291 |
| CTAG1B A_210546_x_at | 3.07 (0.57) | 3.71 (1.80) | 0.0010 |
| CTAG1B A_211674_x_at | 3.44 (0.67) | 3.94 (1.85) | 0.0241 |
| CTAG2 A_215733_x_at | 3.35 (0.50) | 3.81 (1.41) | 0.0048 |
| CTAG1B A_217339_x_at | 3.55 (0.60) | 3.96 (1.42) | 0.0241 |
| MAGEB5 B_234412_at | 3.73 (0.23) | 3.87 (0.25) | 0.0031 |
| | p53 status | | |
| | n = 57 | n = 19 | |
| CTAG1B A_210546_x_at | 3.69 (1.80) | 3.11 (0.71) | 0.0075 |
| CTAG1B A_211674_x_at | 4.04 (1.87) | 3.43 (0.75) | 0.0077 |
| MAGEA A_214612_x_at | 5.14 (1.39) | 4.54 (1.03) | 0.0086 |
| CTAG2 A_215733_x_at | 3.90 (1.41) | 3.35 (0.56) | 0.0009 |
| CTAG1B A_217339_x_at | 4.06 (1.45) | 3.55 (0.63) | 0.0048 |

| | Grade 1 (n = 69) | Grade 2 (n = 125) | Grade 3 (n = 55) | p-value |
|---|---|---|---|---|
| | Tumor grade | | | |
| CTAG1B A_210546_x_at | 3.00 (0.38) | 3.16 (0.83) | 3.65 (1.74) | 0.0242 |
| CTAG1B A_211674_x_at | 3.39 (0.42) | 3.45 (0.91) | 4.01 (1.78) | 0.0296 |
| MAGEA A_214612_x_at | 4.59 (1.07) | 4.53 (0.97) | 5.14 (1.49) | 0.0384 |
| CTAG2 A_215733_x_at | 3.32 (0.31) | 3.40 (0.70) | 3.79 (1.39) | 0.0488 |
| CSAG2 A_220445_s_at | 2.70 (0.85) | 2.62 (0.46) | 3.10 (1.33) | 0.0276 |

| | Low (n = 86) | Medium (n = 104) | High (n = 66) | p-value |
|---|---|---|---|---|
| | Tumor proliferative status | | | |
| SSX2 A_210497_x_at | 4.39 (0.41) | 4.38 (0.43) | 4.69 (0.95) | 0.0276 |
| CTAG1B A_210546_x_at | 3.16 (0.61) | 3.05 (0.62) | 3.63 (1.79) | 0.0276 |
| CTAG1B A_211674_x_at | 3.53 (0.66) | 3.33 (0.65) | 3.99 (1.85) | 0.0163 |
| CTAG2 A_215733_x_at | 3.39 (0.42) | 3.32 (0.62) | 3.83 (1.37) | 0.0077 |
| CSAG2 A_220445_s_at | 2.65 (0.50) | 2.62 (0.66) | 3.07 (1.28) | 0.0241 |
| MAGEB5 B_234412_at | 3.77 (0.24) | 3.71 (0.21) | 3.85 (0.26) | 0.0276 |

TABLE 9

Distant metastasis-free survival (DMFS) rates in 4 patient subgroups from the Uppsala cohort expressing CT-X and correlation of CT-X expression and proliferation rate.

| Affymetrix ID | Gene name | Gene symbol | Correlation with proliferation | UPP_AP DMFS mean_pvals (n = 251) | UPP_AP DMFS mean · hr | UPP_ER_pos DMFS mean_pvals (n = 213) |
|---|---|---|---|---|---|---|
| 206626_x_at | Synovial sarcoma, X breakpoint 1 | SSX1 | 0.155 | 1.20E−01 | 0.405 | 7.83E−02 |
| 209942_x_at | Melanoma antigen family A, 3 | MAGEA3 | 0.173 | 4.54E−02 | 0.492 | 1.59E−01 |
| 210437_at | Melanoma antigen family A, 9 | MAGEA9 | 0.151 | 3.06E−01 | 0.251 | 1.64E−01 |
| 210497_x_at | Synovial sarcoma, X breakpoint 2 | SSX2 | 0.148 | 7.63E−02 | 0.434 | 2.34E−01 |
| 210546_x_at | Cancer/testis antigen 1B | CTAG1B | 0.157 | 3.99E−01 | 0.217 | 6.14E−01 |
| 211670_x_at | Synovial sarcoma, X breakpoint 3 | SSX3 | 0.01 | 5.41E−01 | −0.152 | 1.99E−01 |
| 215733_x_at | Cancer/testis antigen 2 | CTAG2 | 0.183 | 2.80E−01 | 0.278 | 2.20E−01 |
| 224379_at | Ferritin, heavy polypeptide-like 17 | FTHL17 | −0.001 | 3.67E−02 | −0.551 | 8.91E−03 |
| A.207337_at | Cancer/testis antigen 2 | CTAG2 | −0.036 | 5.19E−01 | 0.158 | 6.59E−01 |
| A.208528_x_at | Synovial sarcoma, X breakpoint 5 | SSX5 | −0.088 | 9.61E−02 | 0.407 | 8.38E−02 |
| A.214642_x_at | Melanoma antigen family A, 5 | MAGEA5 | 0.092 | 7.81E−02 | 0.454 | 1.58E−01 |

| Affymetrix ID | UPP_ER_pos DMFS mean · hr | UPP_ER_pos TT_DMFS mean_pvals (n = 68) | UPP_ER_pos TT_DMFS mean · hr | UPP_LN_neg UT_DMFS mean_pvals (n = 135) | UPP_LN_neg UT_DMFS mean · hr |
|---|---|---|---|---|---|
| 206626_x_at | 0.498 | 8.79E−01 | 0.057 | 7.59E−02 | 0.827 |
| 209942_x_at | 0.371 | 6.78E−01 | 0.155 | 4.49E−02 | 0.827 |
| 210437_at | 0.365 | 6.25E−02 | 0.703 | 4.13E−01 | −0.326 |
| 210497_x_at | 0.312 | 1.23E−01 | 0.583 | 5.90E−01 | 0.212 |
| 210546_x_at | 0.134 | 5.60E−01 | −0.228 | 3.97E−02 | 0.817 |
| 211670_x_at | −0.346 | 6.57E−01 | −0.167 | 6.92E−02 | −0.805 |
| 215733_x_at | 0.321 | 7.97E−01 | 0.103 | 5.16E−02 | 0.785 |
| 224379_at | −0.752 | 6.41E−01 | −0.179 | 4.46E−01 | −0.308 |
| A.207337_at | −0.115 | 7.05E−01 | −0.143 | 1.36E−02 | 1.092 |
| A.208528_x_at | 0.451 | 8.41E−01 | 0.075 | 5.59E−01 | 0.230 |
| A.214642_x_at | 0.385 | 8.60E−01 | 0.066 | 2.59E−02 | 1.040 |

UPP_AP = all patients together regardless of treatment type
UPP_ER_pos = All ER+ patients regardless of treatment
UPP_ER_pos_TT = ER+, Tamoxifen treated patients
UPP_LN_neg_UT = Lymph Node negative, untreated (surgery only) patients

TABLE 10

| Gene symbol | IDs |
|---|---|
| CSAG1 | NM_153478, NM_153479 |
| CSAG2 | NM_004909 |
| CSAGE2 | 220445_s_at |
| CTAG1A | A_23_P148541 |
| CTAG1B | 210546_x_at, 211674_x_at, 217339_x_at, NM_001327 |
| CTAG2 | A_23_P22693, 207337_at, 215733_x_at, NM_020994, NM_172377 |
| CXorf48 | 221121_at |
| DDX53 | NM_182699 |
| FATE1 | A_23_P22565, NM_033085 |
| FMR1NB | NM_152578 |
| FTHL17 | A_23_P148410, NM_031894 |
| GAGE1 | 208283_at, NM_001468 |

TABLE 10-continued

| Gene symbol | IDs |
|---|---|
| GAGE2 | 207739_s_at, NM_001472 |
| GAGE3 | 207663_x_at |
| GAGE4 | A_23_P217196, NM_001474 |
| GAGE5 | 207086_x_at, NM_001475 |
| GAGE6 | 208155_x_at, NM_001476 |
| GAGE7 | 208235_x_at, NM_021123 |
| GAGE7B | 206640_x_at |
| GAGE8 | NM_012196 |
| LUZP4 | A_23_P96611, 220665_at, NM_016383 |
| MAGEA1 | A_23_P96295, 207325_x_at, NM_004988 |
| MAGEA10 | A_23_P137007, 210295_at, 214642_x_at, NM_0010115, NM_021048 |
| MAGEA11 | A_23_P113553, 210503_at, NM_005366 |
| MAGEA12 | A_23_P252928, 210467_x_at, NM_005367 |
| MAGEA2 | NM_005361, NM_175742, NM_175743 |
| MAGEA2B | A_23_P148255, 214603_at |
| MAGEA3 | A_23_P62095, 209942_x_at, NM_005362 |
| MAGEA4 | A_23_P171175, 214254_at, NM_002362, NM_0010115, NM_0010115, NM_0010115 |
| MAGEA5 | A_23_P148399, NM_021049 |
| MAGEA6 | A_23_P136870, 214612_x_at, NM_005363, NM_175868 |
| MAGEA8 | A_23_P217554, 210274_at, NM_005364 |
| MAGEA9 | A_23_P85094, 210437_at, NM_005365 |
| MAGEB1 | A_23_P217341, 207534_at, NM_177404, NM_177415, NM_002363 |
| MAGEB2 | 206218_at, A_23_P254831, NM_002364 |
| MAGEB3 | A_23_P96432, 207579_at |
| MAGEB4 | 207580_at, 207581_s_at |
| MAGEB5 | XM_293407 |
| MAGEB6 | NM_173523 |
| MAGEC1 | A_23_P217178, 206609_at, NM_005462 |
| MAGEC2 | A_23_P62099 215932_at 220062_s_at |
| MAGEC3 | 216592_at, NM_138702, NM_177456 |
| PAGE5 | A_23_P22744, NM_130467 |
| SAGE1 | A_23_P21943, A_23_P33343, 220793_at, NM_018666 |
| SPANXA1 | A_23_P96300, 220921_at, 220922_s_at, NM_013453 |
| SPANXB1 | NM_032461 |
| SPANXB2 | A_23_P136883 |
| SPANXC | A_23_P257882, 220217_x_at, NM_022661 |
| SPANXD | A_23_P73498, NM_032417 |
| SSX1 | 206626_x_at, 206627_s_at, NM_005635 |
| SSX2 | 207493_x_at, 210497_x_at, NM_003147, NM_175698 A_23_P252025, A_23_P114133, 207666_x_at, 211670_x_at, 211731_x_at, |
| SSX3 | 215881_x_at, 215885_at, NM_175711, NM_021014 |
| SSX4 | A_23_P254202, 208586_s_at, 210394_x_at, NM_005636, NM_175729 |
| SSX4B | 211425_x_at |
| SSX5 | A_23_P84367, 208528_x_at |
| SSX6 | A_23_P33881 |
| TFDP3 | 207385_at |
| XAGE1 | 220057_at, NM_133430, NM_133431, NM_020411 |
| XAGE2 | A_23_P34031, NM_130777 |
| XAGE3 | A_23_P114343, NM_133179, NM_130776 |

TABLE 11

Breast Cancer Gene Expression Datasets used

| Author | Reference | Microarray | ER− | ER+ | Grade, p53 |
|---|---|---|---|---|---|
| Chin K., et al. | (29) | Affymetrix | 58 | 115 | available |
| Neve R. M., et al. | (28) | Affymetrix | 32 | 19 | NA |
| Hu Z., et al. | (24) | Agilent | 50 | 53 | NA |
| Doane A. S., et al. | (30) | Affymetrix | 41 | 56 | NA |
| vandeVijer M. J., et al.* | (32) | Agilent | 69 | 226 | NA |
| Ivshina A. V., et al.* | (25) | Affymetrix | 34 | 211 | available |
| Miller L. D.., et al. | (27) | Affymetrix | 34 | 213 | available |
| Desmedt C., et al.* | (34) | Affymetrix | 64 | 134 | NA |
| Minn A. J., et al.* | (31) | Affymetrix | 42 | 57 | NA |
| Wang Y., et al.* | (33) | Affymetrix | 77 | 209 | NA |
| Sortiriou C., et al.* | (26) | Affymetrix | 34 | 75 | available |

Each of the foregoing patents, patent applications and references that are recited in this application are herein incorporated in their entirety by reference, particularly for the teaching referenced herein. Having thus described several aspects of embodiments of this invention, it is to be appreciated various alterations, modifications, and improvements will readily occur to those skilled in the art in view of the teachings set forth herein. Such alterations, modifications, and improvements are intended to be part of this disclosure, and are intended to be within the spirit and scope of the invention. Accordingly, the description and drawings are by way of example only.

What is claimed is:

1. A method for treating breast cancer, comprising
   (i) determining the expression of estrogen receptor (ER) and progesterone receptor (PR) in cells of a breast tumor obtained from a subject, and
   (ii) administering to the subject having the breast tumor that is estrogen receptor and progesterone receptor negative (ER/PR-negative) an amount of one or more of a MAGE antigen protein, a CTAG1b antigen protein, or a CTAG2 antigen protein or one or more immunogenic peptides of a MAGE antigen protein, a CTAG1b antigen protein, or a CTAG2 antigen protein, wherein the breast tumor expresses one or more of the MAGE antigen protein, the CTAG 1b antigen protein, or the CTAG2 antigen protein and the amount is effective to induce or increase an immune response against the one or more proteins and/or peptides.

2. The method of claim 1, wherein the breast tumor also is c-erbB2 negative.

3. The method of claim 1, wherein the breast tumor also has p53 mutations.

4. The method of claim 1, further comprising testing a biological sample of the subject during and/or after therapy for the presence of tumor cells.

5. The method of claim 4, wherein the biological sample is a breast tissue biopsy, blood or bone marrow.

6. The method of claim 4, wherein the presence of tumor cells is detected by immunohistochemistry or gene expression analysis.

7. The method of claim 6, wherein the analysis of gene expression is performed using polymerase chain reaction or microarray analysis.

8. The method of claim 1, wherein the MAGE antigen, the CTAG1b antigen, or the CTAG2 antigen or immunogenic peptide of the MAGE antigen, the CTAG 1b antigen, or the CTAG2 antigen is administered as part of a composition, the composition further comprising an adjuvant.

9. The method of claim 8, wherein the adjuvant is selected from MPL, QS21, or a water-in-oil emulsion prepared from squalene and/or tocopherol.

10. The method of claim 8, further comprising administering one or more additional agents that stimulate and/or potentiate the immune response in the subject.

11. The method of claim 1, wherein two or more of the MAGE antigen, the CTAG1b antigen, or the CTAG2 antigen or immunogenic peptides of the MAGE antigen, the CTAG1b antigen, or the CTAG2 antigen are joined together to form a polytope.

12. The method of claim 1, further comprising determining the expression of c-erbB2 in cells of the breast tumor, and/or determining the mutation status of p53 in cells of the breast tumor.

13. The method of claim 12, wherein the mutation status of p53 in cells of the breast tumor is detected using polymerase chain reaction, nucleic acid sequencing, or microarray analysis and/or the expression of c-erbB2 is detected by immunohistochemistry or analysis of gene expression.

14. The method of claim 13, wherein the analysis of gene expression is performed using polymerase chain reaction or microarray analysis.

15. The method of claim 1, wherein the expression of ER and PR in the cells of the breast tumor is determined by immunohistochemistry or analysis of gene expression.

16. The method of claim 15, wherein the analysis of gene expression is performed using polymerase chain reaction or microarray analysis.

17. The method of claim 1, further comprising determining the expression of a MAGE antigen protein, a CTAG1b antigen protein, or a CTAG2 antigen protein in cells of the breast tumor.

18. The method of claim 17, wherein the expression of the MAGE antigen protein, the CTAG1b antigen protein, or the CTAG2 antigen protein in the cells of the breast tumor is detected by immunohistochemistry or analysis of protein expression.

* * * * *